United States Patent
Brancazio et al.

(10) Patent No.: US 11,911,719 B2
(45) Date of Patent: Feb. 27, 2024

(54) DEVICES AND METHODS FOR THE INTEGRATED FILTRATION, DRYING, AND MECHANICAL PROCESSING OF ACTIVE PHARMACEUTICAL INGREDIENTS

(71) Applicant: Massachusetts Institute of Technology, Cambridge, MA (US)

(72) Inventors: David Brancazio, Cambridge, MA (US); Allan S. Myerson, Cambridge, MA (US); Mohammad A. Azad, Greensboro, NC (US); Gregory J. Hammersmith, Windsor, CT (US); Gerard Capellades Mendez, Cambridge, MA (US); Clemence Neurohr, Cambridge, MA (US); Kersten Rapp, Medway, MA (US); Naomi Elizabeth Barbara Briggs, Rockville, MD (US)

(73) Assignee: Massachusetts Institute of Technology, Cambridge, MA (US)

( * ) Notice: Subject to any disclaimer, the term of this patent is extended or adjusted under 35 U.S.C. 154(b) by 22 days.

(21) Appl. No.: 16/933,158

(22) Filed: Jul. 20, 2020

(65) Prior Publication Data
US 2021/0086112 A1  Mar. 25, 2021

Related U.S. Application Data

(60) Provisional application No. 62/904,240, filed on Sep. 23, 2019, provisional application No. 62/903,571, filed on Sep. 20, 2019.

(51) Int. Cl.
*B01D 29/86* (2006.01)
*A61K 31/496* (2006.01)
(Continued)

(52) U.S. Cl.
CPC .......... *B01D 29/86* (2013.01); *A61K 31/496* (2013.01); *B01D 29/05* (2013.01); *B01D 29/608* (2013.01);
(Continued)

(58) Field of Classification Search
None
See application file for complete search history.

(56) References Cited

U.S. PATENT DOCUMENTS

| 207,283 | A | * | 8/1878 | Kaestner | ............. | B01F 7/00208 |
|---|---|---|---|---|---|---|
| | | | | | | 366/312 |
| 415,796 | A | * | 11/1889 | Rieseck | ............... | B65G 47/846 |
| | | | | | | 198/723 |

(Continued)

FOREIGN PATENT DOCUMENTS

| CH | 669 533 A5 | 3/1989 |
|---|---|---|
| CN | 204656096 U | 9/2015 |

(Continued)

OTHER PUBLICATIONS

International Search Report and Written Opinion dated Nov. 16, 2020 in connection with PCT/US2020/046635.
(Continued)

*Primary Examiner* — Robert J Popovics
(74) *Attorney, Agent, or Firm* — Wolf, Greenfield & Sacks, P.C.

(57) ABSTRACT

Devices and methods for filtering, drying, and mechanically processing active pharmaceutical ingredients are generally described.

19 Claims, 28 Drawing Sheets

(51) Int. Cl.
    *B01D 29/05*           (2006.01)
    *B01D 29/60*           (2006.01)
    *B01D 35/18*           (2006.01)
    *A61J 3/10*            (2006.01)
    *B01D 29/075*         (2006.01)

(52) U.S. Cl.
    CPC ............... B01D 35/18 (2013.01); *A61J 3/10* (2013.01); *B01D 29/075* (2021.08); *B01D 2201/204* (2013.01)

(56) References Cited

U.S. PATENT DOCUMENTS

| | | | | |
|---|---|---|---|---|
| 442,081 A * | 12/1890 | Nelson | B01F 3/04531 | 366/170.3 |
| 442,213 A * | 12/1890 | Young | A23G 9/12 | 366/149 |
| 553,191 A * | 1/1896 | Frasch | B01F 7/00208 | 366/312 |
| 624,633 A * | 5/1899 | Edwardes | B01D 21/0012 | 210/330 |
| 684,555 A * | 10/1901 | Simpson | B01D 29/05 | 210/414 |
| 726,911 A * | 5/1903 | Hasenbach | B01F 7/162 | 366/314 |
| 733,471 A * | 7/1903 | Ellis | B01F 7/1675 | 366/306 |
| 1,184,339 A * | 5/1916 | Fowler | B01F 13/002 | 366/343 |
| 1,428,965 A * | 9/1922 | Lane | B01J 23/70 | 422/225 |
| 1,567,990 A * | 12/1925 | Apablasa | B01D 29/6476 | 210/120 |
| 1,574,557 A * | 2/1926 | Coe | B01D 35/14 | 210/272 |
| 1,638,471 A * | 8/1927 | Carveth | B01J 10/005 | 423/622 |
| 1,689,277 A * | 10/1928 | Burns | B01D 29/23 | 210/408 |
| 1,741,444 A * | 12/1929 | Slider | B01D 29/01 | 210/355 |
| 2,089,702 A * | 8/1937 | Lomax | A23B 5/00 | 210/408 |
| 2,107,040 A * | 2/1938 | Lomax | A23B 5/00 | 426/495 |
| 2,960,226 A * | 11/1960 | Ekstrom, Jr. | B03B 5/623 | 209/158 |
| 3,034,895 A * | 5/1962 | O'Malley | C12C 7/065 | 426/436 |
| 3,055,208 A * | 9/1962 | Gallus | B01D 29/03 | 210/415 |
| 3,380,373 A * | 4/1968 | Lenz | C12C 7/161 | 99/278 |
| 3,441,141 A * | 4/1969 | Eicher | B01D 29/70 | 210/241 |
| 3,456,708 A * | 7/1969 | Strandell | F26B 11/14 | 209/11 |
| 3,594,991 A * | 7/1971 | Berz | B01D 46/30 | 55/294 |
| 3,743,539 A * | 7/1973 | Kroyer | B01D 9/0031 | 127/16 |
| 3,836,464 A * | 9/1974 | Brookins | B01D 29/666 | 210/413 |
| 3,871,846 A * | 3/1975 | Berz | B01D 46/30 | 55/303 |
| 3,917,472 A * | 11/1975 | Berz | B01D 50/00 | 55/282 |
| 4,081,381 A * | 3/1978 | Rosenmund | B01D 29/84 | 210/408 |
| 4,163,723 A * | 8/1979 | Romano | B03B 5/36 | 209/159 |
| 4,376,705 A * | 3/1983 | Komura | B01D 29/86 | 210/413 |
| 4,399,042 A * | 8/1983 | Stannard | B01D 29/445 | 210/791 |
| 4,417,980 A * | 11/1983 | Baur | B01D 29/86 | 210/91 |
| 4,465,376 A * | 8/1984 | Baumgartner | B01F 7/165 | 34/173 |
| 4,542,682 A * | 9/1985 | Hancock | C12C 7/17 | 99/277.1 |
| 4,592,835 A * | 6/1986 | Grieder | B01D 29/01 | 210/107 |
| 4,631,026 A * | 12/1986 | McKinney | F27B 9/16 | 414/158 |
| 4,696,433 A * | 9/1987 | Lenz | C12C 7/17 | 241/199.12 |
| 4,828,697 A * | 5/1989 | Kuhnt | B01D 29/055 | 210/408 |
| 4,888,111 A * | 12/1989 | Diemer | B01D 35/16 | 210/178 |
| 4,975,183 A * | 12/1990 | Glorer | B01D 29/6476 | 210/107 |
| 4,990,346 A * | 2/1991 | Strippier | C12C 7/14 | 426/231 |
| 4,992,171 A * | 2/1991 | Hetzel | B01D 29/6476 | 210/413 |
| 5,071,546 A * | 12/1991 | Ruegg | B01D 29/6476 | 210/148 |
| 5,139,667 A * | 8/1992 | Reneau, Jr. | B01D 29/86 | 210/319 |
| 5,143,630 A * | 9/1992 | Rolchigo | B01D 29/055 | 210/780 |
| 5,259,955 A * | 11/1993 | Bolton | B01D 29/118 | 210/406 |
| 5,269,923 A * | 12/1993 | Diemer | B01D 29/86 | 210/413 |
| 5,544,424 A * | 8/1996 | Haleen | F26B 3/092 | 34/166 |
| 5,544,425 A * | 8/1996 | Haleen | F26B 11/14 | 34/166 |
| 5,546,676 A * | 8/1996 | Haleen | F26B 3/092 | 34/166 |
| 5,564,350 A * | 10/1996 | Peplinski | B01D 29/86 | 110/259 |
| 5,614,093 A * | 3/1997 | Mueggenburg | B01D 29/018 | 210/355 |
| 5,653,869 A * | 8/1997 | Evangelisti | B01D 29/05 | 210/232 |
| 5,659,971 A * | 8/1997 | Haleen | F26B 11/14 | 34/166 |
| 5,709,036 A * | 1/1998 | Haleen | F26B 3/092 | 34/95 |
| 5,746,007 A * | 5/1998 | Haleen | F26B 21/14 | 34/166 |
| 5,794,518 A * | 8/1998 | Stippler | C12C 7/14 | 426/29 |
| 6,167,637 B1 * | 1/2001 | Nagase | B01D 29/09 | 34/388 |
| 6,890,129 B2 * | 5/2005 | Fabbri | F26B 25/002 | 406/146 |
| 6,959,504 B2 * | 11/2005 | Fabbri | B08B 9/0933 | 34/179 |
| 7,020,984 B2 * | 4/2006 | Knorr | F26B 11/14 | 34/594 |
| 7,473,375 B2 * | 1/2009 | Stoerzer | B01D 29/94 | 210/791 |
| 7,708,257 B2 * | 5/2010 | Schmidt | F26B 25/04 | 416/223 R |
| 7,713,411 B2 * | 5/2010 | Banister | F26B 3/08 | 210/791 |
| 8,597,509 B2 * | 12/2013 | Knight | B01D 15/1807 | 210/198.2 |
| 9,211,512 B2 * | 12/2015 | Kim | B01F 13/0059 | |
| 9,713,778 B2 * | 7/2017 | Knight | B01D 15/1807 | |
| 10,155,786 B2 | 12/2018 | Myerson et al. | | |
| 10,702,481 B2 * | 7/2020 | Myerson | B30B 15/302 | |

(56) References Cited

U.S. PATENT DOCUMENTS

| | | | | |
|---|---|---|---|---|
| 10,858,303 | B1* | 12/2020 | Ferraro | C07C 37/84 |
| 11,020,352 | B2* | 6/2021 | Myerson | A61K 31/5513 |
| 11,103,812 | B2* | 8/2021 | Canaia | B29C 48/693 |
| 2003/0000101 | A1* | 1/2003 | Fabbri | B01D 29/01 34/380 |
| 2003/0000103 | A1* | 1/2003 | Fabbri | B01D 29/843 34/576 |
| 2004/0028765 | A1* | 2/2004 | Kerzner | A61J 3/10 425/352 |
| 2004/0159007 | A1* | 8/2004 | Knorr | B01J 2/10 34/593 |
| 2006/0062079 | A1* | 3/2006 | Schmidt | B01F 35/55 366/325.1 |
| 2008/0173594 | A1* | 7/2008 | Stoerzer | B01D 29/01 210/791 |
| 2014/0224749 | A1* | 8/2014 | Hopkins | B29C 48/69 210/791 |
| 2016/0317953 | A1* | 11/2016 | Canaia | B29C 48/693 |
| 2017/0282420 | A1* | 10/2017 | Kitamura | B29C 43/34 |
| 2017/0312674 | A1 | 11/2017 | Myerson et al. | |
| 2018/0161706 | A1* | 6/2018 | Masetto | B01D 29/05 |
| 2018/0207604 | A1 | 7/2018 | Jensen et al. | |
| 2018/0271791 | A1* | 9/2018 | Myerson | B29C 43/34 |
| 2020/0352865 | A1* | 11/2020 | Myerson | A61K 31/192 |
| 2021/0086112 | A1* | 3/2021 | Brancazio | B01D 29/86 |
| 2022/0305448 | A1* | 9/2022 | Zhang | B01F 27/92 |

FOREIGN PATENT DOCUMENTS

| | | | |
|---|---|---|---|
| CN | 108176095 A | 6/2018 | |
| CN | 108176101 A | 6/2018 | |
| CN | 109173325 A | 1/2019 | |
| GB | 251398 A * | 5/1926 | B01D 24/105 |
| WO | WO 2018/152320 A1 | 8/2018 | |

OTHER PUBLICATIONS

[No Author Listed], Agitated Nutsche Filter and Filter-Dryer. De Dietrich. Oct. 29, 2016. Accessed Jan. 28, 2021 as available Oct. 29, 2016 from < https://web.archive.org/web/20161029070212/http://www.dedietrich.com:80/en/solutions-and-products/liquid-solid-separation/agitated-nutsche-filter-and-filter-dryer>. 8 pages.

[No Author Listed], Agitated Nutsche Filters, Filter-Dryers. Heinkel. Dec. 18, 2014. Accessed Jan. 28, 2021 as available Dec. 18, 2014 from < https://web.archive.org/web/20141218045548/http://www.heinkel.com/products/nutsche-filters-en-filter-dryers/nutsche-filters-en-filter-dryers-pharma.aspx>. 3 pages.

[No Author Listed], Agitated Nutsche Filter Dryer (ANFD). Millennium Equipments (P) Ltd. Jan. 3, 2013. Accessed Jan. 28, 2021 as available Jan. 3, 2013 from < https://web.archive.org/web/20130103041748/http://www.millenniumequipments.com/anfd.html >. 4 pages.

[No Author Listed], Agitated Nutsche Filter Dryers: optimum performance, quality and safety. Manufacturing Chemist. Jul. 16, 2014. Accessed Jan. 28, 2021 from <https://www.manufacturingchemist.com/news/article_page/Agitated_Nutsche_Filter_Dryers_optimum_performance_quality_and_safety/99298>. 6 pages.

[No Author Listed], PAT—A Framework for Innovative Pharmaceutical Development, Manufacturing, and Quality Assurance. US FDS. Sep. 2004 Retrieved from < https://www.fda.gov/media/71012/download>. 19 pages.

Abdullah et al., The use of bulk density measurements as flowability indicators. Powder Technol. Mar. 3, 1999;102(2):151-165.

Acevedo et al., Evaluation of mixed suspension mixed product removal crystallization processes coupled with a continuous filtration system. Chem Eng Process Process Intensif. Oct. 2016;108:212-9. doi:10.1016/j.cep.2016.08.006.

Adamo et al., On-demand continuous-flow production of pharmaceuticals in a compact, reconfigurable system. Science. Apr. 2016;352(6281):61-7.

Alvarez et al., Crystallization of Cyclosporine in a Multistage Continuous MSMPR Crystallizer. Cryst Growth Des. 2011;11(10):4392-400. Epub Aug. 10, 2011.

Azad et al., A compact, portable, re-configurable, and automated system for on-demand pharmaceutical tablet manufacturing. Int J Pharm. Mar. 25, 2018;539(1-2):157-164. Epub Jan. 31, 2018. Manuscript provided, 37 pages.

Capellades et al., Mixed-Suspension, Mixed-Product Removal Studies of Ciprofloxacin from Pure and Crude Active Pharmaceutical Ingredients: The Role of Impurities on Solubility and Kinetics. Cryst Growth Des. Jul. 3, 2019;19(7):4008-18. Epub May 31, 2019. doi:10.1021/acs.cgd.9b00400.

Chen et al., Particle Size Reduction Studies on the Lab and Commercial Scale using High and Low Energy Mills. Am Pharm Rev. Apr. 1, 2012. Retrieved online from <https://www.americanpharmaceuticalreview.com/Featured-Articles/112359-Particle-Size-Reduction-Studies-on-the-Lab-and-Commercial-Scale-using-High-and-Low-Energy-Mills/>. Accessed Apr. 2, 2021. 4 pages.

Cypes et al., Drying an organic monohydrate: Crystal form instabilities and a factory-scale drying scheme to ensure monohydrate preservation. Org Process Res Dev. May 2004;8(4):576-582. doi:10.1021/op049956a.

Deng et al., Effect of calcium oxide (CaO) and sawdust on adhesion and cohesion characteristics of sewage sludge under agitated and non-agitated drying conditions. Water Res. Mar. 1, 2017;110:150-160. doi:10.1016/j.watres.2016.12.001.

Diorazio et al., Toward a more holistic framework for solvent selection. Org Process Res Dev. Feb. 18, 2016;20(4):760-73. Epub Mar. 14, 2016.

Freeman, Measuring the flow properties of consolidated, conditioned and aerated powders—a comparative study using a powder rheometer and a rotational shear cell. Powder Technol. May 16, 2007;174(1-2): 25-33.

Fukunaka et al., Effect of particle shape of active pharmaceutical ingredients prepared by fluidized-bed jet-milling on cohesiveness. J Pharm Sci. May 2005;94(5):1004-12. doi: 10.1002/jps.20307.

Gouveia et al., Using PAT to accelerate the transition to continuous API manufacturing. Anal Bioanal Chem. Jan. 2017;409(3):821-832. doi: 10.1007/s00216-016-9834-z. Epub Aug. 11, 2016.

Gutmann et al., Continuous-flow technology—A tool for the safe manufacturing of Active Pharmaceutical Ingredients. Angew Chem Int Ed. May 18, 2015;54(23):6688-728. doi:10.1002/anie.201409318.

Hartman et al., Deciding whether to go with the flow: Evaluating the merits of flow reactors for synthesis. Angew Chem Int Ed Engl. Aug. 8, 2011;50(33):7502-19. doi: 10.1002/anie.201004637. Epub Jun. 27, 2011.

Ho et al., Effect of milling on particle shape and surface energy heterogeneity of needle-shaped crystals. Pharm Res. Oct. 2012;29(10):2806-16. doi: 10.1007/s11095-012-0842-1. Epub Aug. 8, 2012.

Jimenez-Gonzales et al., Key Green Engineering Research Areas for Sustainable Manufacturing: A Perspective from Pharmaceutical and Fine Chemicals Manufacturers. Org Process Res Dev. Feb. 22, 2011;15(4):900-11. Epub Feb. 22, 2011.

Knieke et al., Sub-100 micron fast dissolving nanocomposite drug powders. Powder Technol. Feb. 2015;271:49-60.

Lee, Current FDA Perspective for Continuous Manufacturing. In: MIT-CMAC 2nd International Symposium on Continuous Manufacturing of Pharmaceuticals. Sep. 26-27, 2016. <http://qbdworks.com/wp-content/uploads/2014/06/FDA-on-Continuous-Manufacturing-Lee-2016.pdf>. 18 pages.

Lim et al., Understanding and preventing agglomeration in a filter drying process. Powder Technol. Oct. 2006;300:146-56. doi:10.1016/j.powtec.2016.03.003.

Lovette et al., Needle-shaped crystals: Causality and solvent selection guidance based on periodic bond chains. Cryst Growth Des. 2013;13(8):3341-3352. doi:10.1021/cg301830u.

MacLeod et al., On the fracture of pharmaceutical needle-shaped crystals during pressure filtration: case studies and mechanistic understanding. Org Process Res Dev. Feb. 2, 2012;16(3):425-34. Epub Feb. 27, 2012.

(56) References Cited

OTHER PUBLICATIONS

Ottoboni et al., Development of a Novel Continuous Filtration Unit for Pharmaceutical Process Development and Manufacturing. J Pharm Sci. 2019;108(1):372-381. doi:10.1016/j.xphs.2018.07.005.
Plumb, Continuous Processing in the Pharmaceutical Industry. Chem Eng Res Des. 2005;83(6):730-38. doi:10.1205/cherd.04359.
Poechlauer et al., Continuous processing in the manufacture of active pharmaceutical ingredients and finished dosage forms: an industry perspective. Org Process Res Dev. 2012;16:1586-1590.
Rathore, Roadmap for implementation of quality by design (QbD) for biotechnology products. Trends in Biotechnol. Sep. 2009;27(9):546-53. doi: 10.1016/j.tibtech.2009.06.006.
Schaber et al., Economic Analysis of Integrated Continuous and Batch Pharmaceutical Manufacturing: A Case Study. Ind Eng Chem Res. Jul. 27, 2011;50(17):10083-92. doi:10.1021/ie2006752.
Shekunov et al., Particle size analysis in pharmaceutics: principles, methods and applications. Pharm Res. Feb. 2007;24(2):203-27. doi: 10.1007/s11095-006-9146-7. Epub Dec. 27, 2006.
Wilson et al., Particle engineering of needle shaped crystals by wet milling and temperature cycling: Optimisation for roller compaction. Powder Technol. Nov. 2018;339:641-650.
Wong et al., Compact Crystallization, Filtration, and Drying for the Production of Active Pharmaceutical Ingredients. Org Process Res Dev. Mar. 17, 2013;17(4):684-692. doi:10.1021/op400011s. Epub Apr. 2, 2013.
Wu et al., Image analytical approach for needle-shaped crystal counting and length estimation. Crystal Growth & Design. Sep. 3, 2018;15(10):4876-4885. Epub Sep. 17, 2015.
Yu et al., The Effect of Temperature and pH on the Solubility of Quinolone Compounds: Estimation of Heat of Fusion. Pharm Res. Apr. 1994;11(4):522-7. doi: 10.1023/a:1018910431216.
Yu et al., Understanding Pharmaceutical Quality by Design. AAPS J. Jul. 2014;16(4):771-83. Epub May 23, 2014. doi: 10.1208/s12248-014-9598-3.
Zhang et al., Advanced Continuous Flow Platform for On-Demand Pharmaceutical Manufacturing. Chemistry. Feb. 21, 2018;24(11):2776-2784. Epub Jan. 31, 2018. doi: 10.1002/chem.201706004.
Chinese Office Action dated Dec. 14, 2022, for Application No. CN 202080065610.
Capellades et al., A Compact Device for the Integrated Filtration, Drying, and Mechanical Processing of Active Pharmaceutical Ingredients. J Pharm Sci. Mar. 2020;109(3):1365-1372. doi: 10.1016/j.xphs.2019.12.011. Epub Dec. 20, 2019.
Chinese Office Action dated Jun. 21, 2023, for Application No. CN202080065610.3.
European Office Action dated Jun. 28, 2023, for Application No. EP20764260.4.
Decision on Rejection dated Sep. 22, 2023, for Chinese Patent Application No. CN202080065610.3.
Han et al., TRIZ innovation theory and application. Tianjin University Press. Mar. 31, 2020: 81.
Hu, Production and application of a pharmaceutical excipient—thin film coating. China Medical Science Press. May 31, 2014; 117.
Tian, Oil hydrogenation technology. China Light Industry Press. Mar. 31, 1987: 105.

* cited by examiner

DEVICES AND METHODS FOR THE INTEGRATED FILTRATION, DRYING, AND MECHANICAL PROCESSING OF ACTIVE PHARMACEUTICAL INGREDIENTS

RELATED APPLICATIONS

This application claims priority under 35 U.S.C. § 119(e) to U.S. Provisional Application No. 62/903,571, filed Sep. 20, 2019, and entitled "Devices and Methods for the Integrated Filtration, Drying, and Mechanical Processing of Active Pharmaceutical Ingredients," and to U.S. Provisional Application No. 62/904,240, filed Sep. 23, 2019, and entitled "Devices and Methods for the Integrated Filtration, Drying, and Mechanical Processing of Active Pharmaceutical Ingredients," each of which is incorporated herein by reference in its entirety for all purposes.

GOVERNMENT SPONSORSHIP

This invention was made with Government support under Grant No. HR0011-16-2-0029 awarded by the Defense Advanced Research Projects Agency (DARPA). The Government has certain rights in the invention.

TECHNICAL FIELD

Devices and methods for filtering, drying, and/or mechanically processing active pharmaceutical ingredients are generally described.

BACKGROUND

Devices designed for the filtration, washing, drying, de-lumping, and particle size reduction of solid active pharmaceutical ingredients (APIs) in miniaturized continuous processes are useful in the production of pharmaceutical products. In pharmaceutical production, isolation of the API with the desired chemical, physical, and morphological properties requires the integration of several unit operations following crystallization. These are oriented to solids recovery and powder processing to ensure that the recovered API has the right bioavailability and the appropriate properties for drug product formulation.

Nutsche filters have been used to filter pharmaceutical products. However, the use of Nutsche filters can be disadvantageous under certain circumstances. Accordingly, improved devices and methods for filtering APIs would be desirable.

SUMMARY

Devices and methods for filtering, drying, and/or mechanically processing active pharmaceutical ingredients (API) are generally described. Certain embodiments relate to filtration devices and/or uses thereof. In some embodiments, the filtration device comprises a filtration medium and a rotating edge (which may be part of a fin of an impeller) that comprises a plurality of protrusions extending from it. The protrusions may be arranged such that they aid in the breakup of agglomerates and/or crystals of API when the edge sweeps the facial area of the filtration medium. The subject matter of the present invention involves, in some cases, interrelated products, alternative solutions to a particular problem, and/or a plurality of different uses of one or more systems and/or articles.

Certain aspects are related to filtration devices. In some embodiments, the filtration device comprises a filtration medium, and a rotatable edge comprising a plurality of protrusions extending from the edge toward the filtration medium, wherein the rotatable edge is configured to sweep a facial area of the filtration medium during rotation.

In some embodiments, the filtration device comprises a filtration medium and an impeller comprising a shaft and at least one fin, the at least one fin comprising a plurality of protrusions extending toward the filtration medium.

Some aspects are related to methods. In some embodiments, the method comprises rotating an edge comprising a plurality of protrusions extending toward a filtration medium such that the edge sweeps the facial area of the filtration medium.

Certain embodiments are related to methods of processing a composition comprising an active pharmaceutical ingredient. In some embodiments, the method comprises rotating an edge comprising a plurality of protrusions extending toward a filtration medium such that the edge sweeps the filtration medium and breaks up agglomerates and/or lumps comprising the active pharmaceutical ingredient.

In some embodiments, the method comprises rotating an impeller comprising a shaft and at least one fin around a shaft of the impeller such that the at least one fin sweeps a filtration medium, the at least one fin comprising a plurality of protrusions extending toward the filtration medium.

In certain embodiments, the method comprises rotating an impeller comprising a shaft and at least one fin around the shaft of the impeller such that the at least one fin sweeps a filtration medium and breaks up agglomerates and/or lumps comprising the active pharmaceutical ingredient.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present disclosure describes devices and methods for filtering active pharmaceutical ingredients (APIs). Certain aspects describe a filtration device comprising a filtration medium and a rotating edge that comprises a plurality of protrusions extending from the rotating edge toward the filtration medium. Certain aspects describe a method for processing a composition comprising an API. The method may involve rotating the edge comprising the protrusions such that the edge sweeps the filtration medium. In some embodiments, the edge comprising the protrusions can be an edge of a fin that extends from a shaft, the fin and the shaft making up part of a larger impeller. In other embodiments, the edge can be rotated using other methods. In certain cases, the protrusions are arranged such that they aid in the breakup of agglomerates and/or crystals of API when the edge sweeps the facial area of the filtration medium.

In processing an API, it may be necessary to isolate the API from the remaining components of a slurry. The slurry may take any of a variety of forms, but generally includes a mixture of a solid material (e.g., an API) and a liquid material (e.g., a carrier liquid). Examples of slurries include, but are not limited to, colloids and suspensions. In the manufacture and processing of an API, the final step in isolating the API (before, for example, tableting) may be to precipitate the API and wash the API with appropriate solvents or other liquids to assist in obtaining a pure API. The API may then be isolated, typically via filtration. The precipitation and washing of the API can result in the formation of a slurry containing the API. Certain of the devices and methods described herein can be used to isolate an API from a slurry in ways that are advantageous over conventional methods. For example, conventional methods may provide an API of a size or morphology unsuitable for tableting for further processing. In some cases, conventional methods may provide a particle size that is too large or too small. Certain of the devices and methods described herein, however, may provide an isolated API of a certain, desirable particle size range and/or morphology. This can be achieved, for example, by introducing a plurality of protrusions to an edge that sweeps the filtration medium (e.g., on a blade(s) of an impeller configured to sweep the filtration medium) and sweeping the edge across the filtration medium such that the particle size of the API is reduced. Such operation (and associated advantages) are described in more detail below.

Figure 1A:
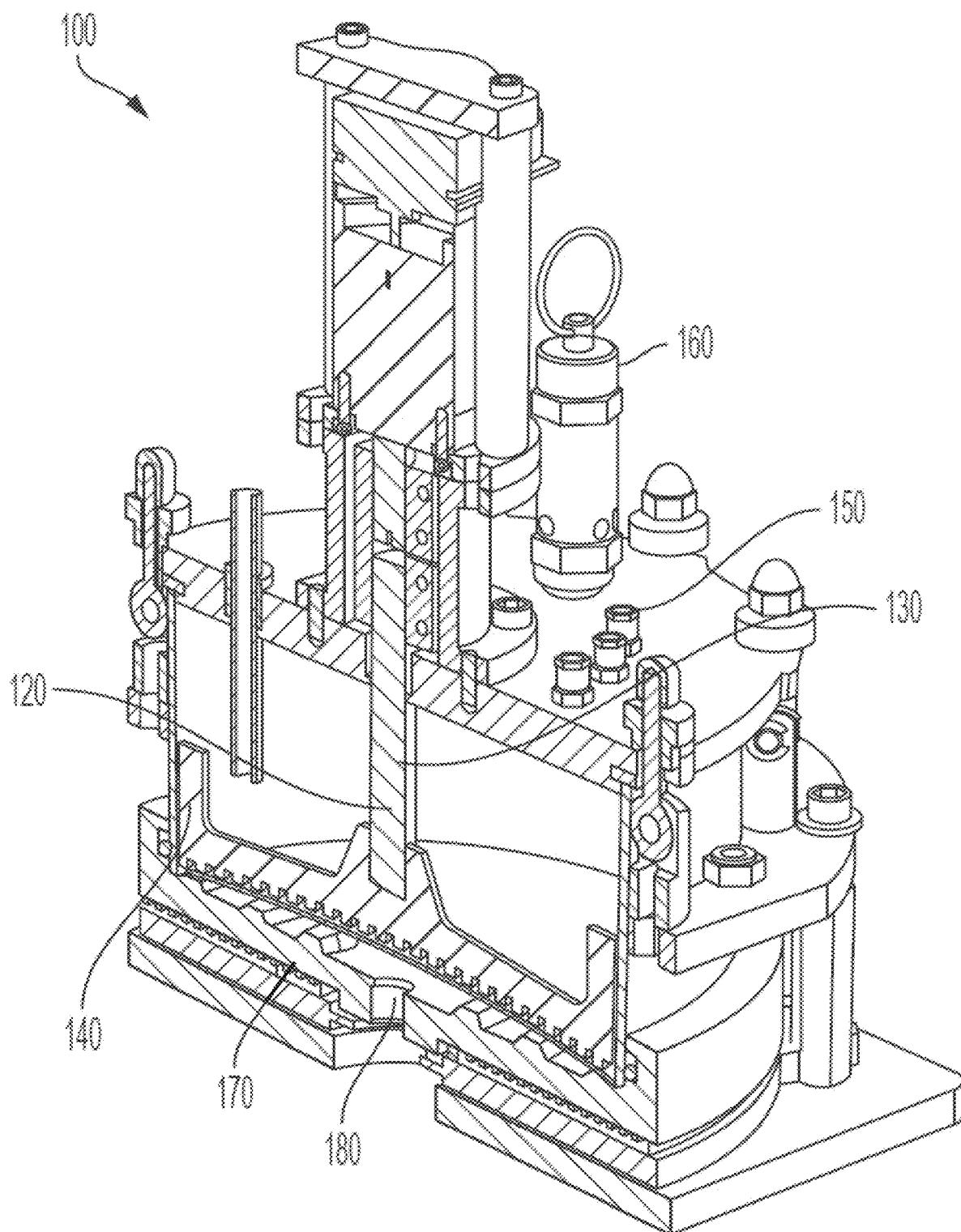
FIG. 1A is a cross-sectional cutaway schematic illustration of a filtration device, according to some embodiments.

As stated above, certain embodiments are related to filtration devices and methods of filtration. FIG. 1A is a schematic illustration of filtration device 100, in accordance with certain embodiments. In some embodiments, the filtration device comprises a filtration medium. For example, in FIG. 1A, filtration device 100 comprises filtration medium 170. The filtration medium generally comprises a porous material that allows the flow of liquid through the filtration medium while retaining at least a portion of the solid particles. The filtration medium may be a mesh, a sieve, a fibrous material, a porous membrane or any other porous material. In some embodiments, the filtration medium may optionally allow comparatively small particles to be transported through while retaining comparatively large particles on the filtration medium. The filtration medium can be used to isolate a solid from a slurry (e.g., a suspension) and/or to isolate a liquid from solid particles.

Figure 1B:
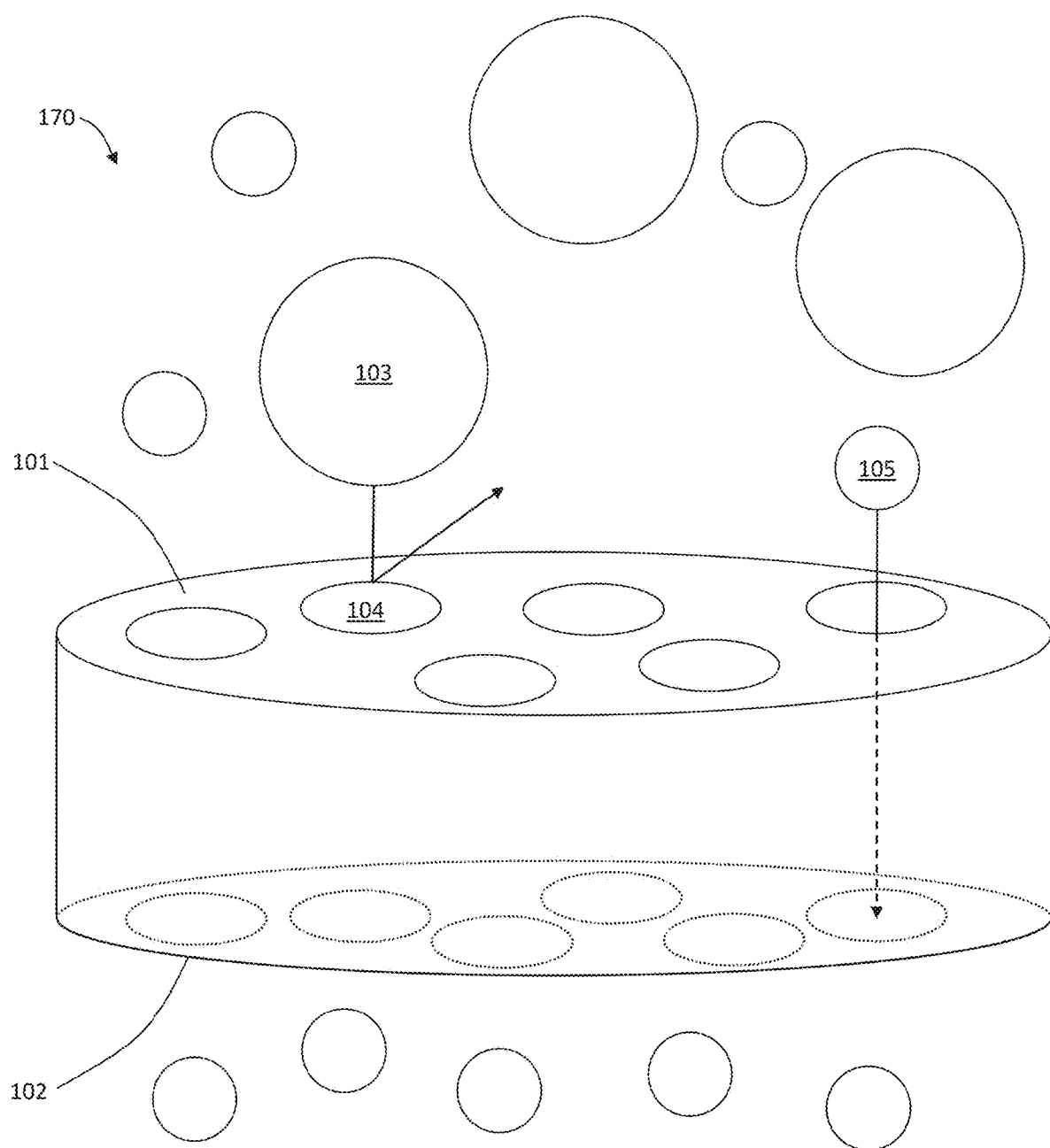
FIG. 1B is a perspective view schematic illustration of a filtration medium, according to certain embodiments.

In some embodiments, particles too large to pass through the pores of the filtration medium are retained within or on top of the filtration medium. Liquids and, optionally, particles smaller than the pores of the filtration medium may be passed through the filtration medium. By way of example and not limitation, FIG. 1B is a schematic illustration of filtration medium 170 with retentate side 101 and permeate side 102 comprising pores 104. Larger particles, such as large particle 103, are too large to pass through pores 104 on retentate side 101. On the other hand, liquid may be freely transported through pores 104. In addition, in some cases, smaller particles, such as small particle 105, with a largest dimension smaller than the pore size of pore 104 may pass from the retentate side 101 to the permeate side 102 via pores 104. In this way, larger particles may be separated from liquid (and, optionally, smaller particles). Upon passing a slurry (e.g., a suspension) through the filtration medium, a solid may be retained by the filtration medium. This solid may be referred to as "retentate," but may also be described as a "retained solid," or a "cake." In some embodiments, the retentate comprises an API that one wishes to isolate.

As described above, the filtration medium may comprise pores. As used herein, a "pore" of an article (e.g., a filtration medium) refers to a conduit, void, or passageway, at least a portion of which is surrounded by the medium in which the pore is formed such that a continuous loop may be drawn around the pore while remaining within the medium. The "porosity" of an article is expressed as a percentage, and is calculated as follows:

$$\text{Porosity} = \frac{V_p}{V_{article}} \times 100\%$$

where $V_p$ is the volume occupied by the pores of the article and $V_{article}$ is the geometric volume of the article. The geometric volume of an article is calculated by measuring the volume of the article as defined by its geometric surfaces, which are the surfaces of the article that define its outer boundaries (for example, the area that may be measured by a macroscopic measuring tool (e.g., a ruler)). Those of ordinary skill in the art would be capable of determining the porosity of a particular article using, for example, mercury intrusion porosimetry.

The filtration medium may comprise pores of a particular pore size. As used herein, the "pore size" of a pore is the shortest distance between two opposite walls of the pore. By way of illustration and not limitation, in the case of a cylindrically-shaped pore, the pore size would be the diameter of the cylinder. The porosity or pore size may be chosen, in certain embodiments, as to select which particles pass through the filtration medium and which particles are retained. In some embodiments, the filtration medium comprises pores having a pore size of at least 0.01 micrometers, at least 0.1 micrometers, at least 0.2 micrometers, or more. In certain embodiments, the filtration medium comprises pores having a pore size of up to 1 micrometer, up to 10 micrometers, or more. Combinations of these ranges are also possible. Other pore sizes are also possible.

In some embodiments, the filtration medium has a porosity of at least 1%, at least 5%, at least 10%, or more. In certain embodiments, the filtration medium has a porosity of up to 50%, or more. Combinations of these ranges are also possible. Other porosities are also possible.

The filtration medium may comprise, for example, any material suitable for isolating an API without unwanted degradation of the medium due to a liquid passing through the filtration medium or by the solid particles retained by the medium (e.g., a solid API). In some embodiments, all or a portion of the filtration medium may be made of a polymer, a metal, a ceramic, or a combination of one or more of these. In some embodiments, the filtration medium may be made from a material that is not reactive with a liquid passing through or solid particles that come into contact with it. Non-limiting examples of suitable filtration medium materials include cellulose fibers, cellulose acetate, mixed cellulose esters, nitrocellulose, glass fibers, nylon, polytetrafluoroethylene (PTFE), polyethersulfone (PES), polyamides, and metals (e.g., stainless steel, hastelloy C-276, etc.). Those of ordinary skill in the art, given the insight provided by the present disclosure, would be capable of choosing a filtration medium having appropriate properties (e.g., materials of manufacture, porosity, etc.) for isolating desired solid particles or particular API.

Figure 1C:
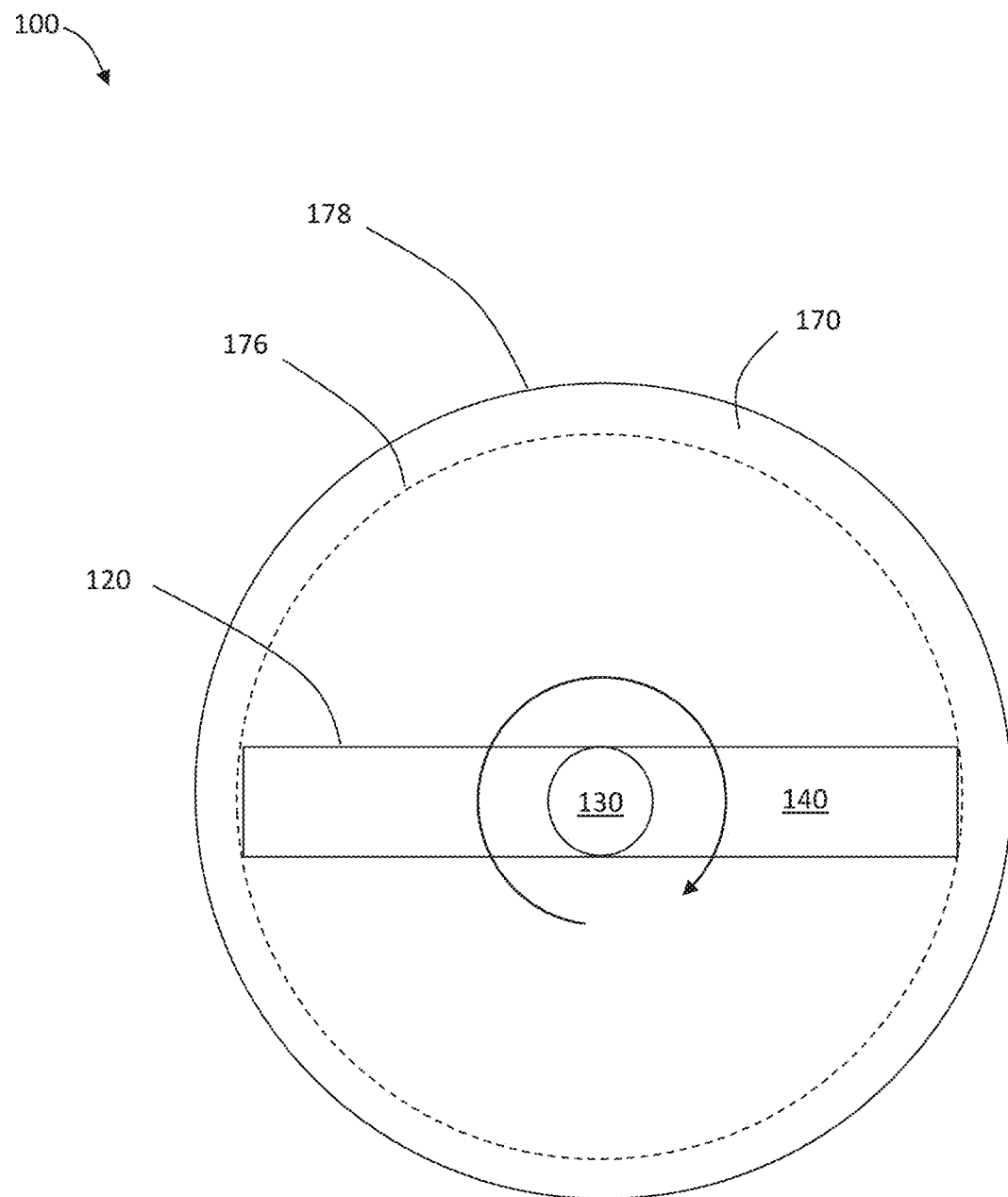
FIG. 1C is a top view schematic illustration of a filtration device comprising fins extending in opposite directions, according to one set of embodiments.

The filtration medium may have any of a variety of suitable dimensions for filtering a slurry (e.g., suspension). In some embodiments, it can be advantageous to use a filtration medium with a relatively small facial area. The facial area of the filtration medium is a mathematical area of the outer boundaries of the geometric surface of the filtration medium, at least a portion of which is swept by the edge comprising the protrusions (as may be found, for example, on an impeller). As would be understood by those of ordinary skill in the art, the geometric surface of the filtration medium refers to the surface that may be measured by a macroscopic measuring tool, such as a ruler, and does not include the internal surface area (e.g., area within pores of the filtration medium, or surface area of any fibers that make up the filtration medium, etc.). FIG. 1C is a top view schematic illustration of filtration device 100. In FIG. 1C, the facial area of filtration medium 170 corresponds to the area within circle 178 (the circle which defines the outer boundaries of filtration medium 170), at least a portion of which (the portion within sweep area 176) is swept by edge 143 of fin 140 as shaft 130 rotates impeller 120.

In some embodiments, the filtration medium has a facial area of less than or equal to 1 m$^2$, less than or equal to 0.1 m$^2$, less than or equal to 0.01 m$^2$, less than or equal to 1000 cm$^2$, less than or equal to 100 cm$^2$, or less. In certain embodiments, the filtration medium has a facial area of as little as 20 cm$^2$, as little as 10 cm$^2$, or less. Combinations of these ranges are also possible. Other facial areas are also possible.

The filtration medium may also have any of a variety of suitable thicknesses. In some embodiments, it can be beneficial to use a filtration medium that is relatively thin (e.g., less than 1 cm, less than 5 mm, or less than 2 mm in thickness), for example, to reduce bulk and overall dimensions of the filtration device.

Figure 1D:
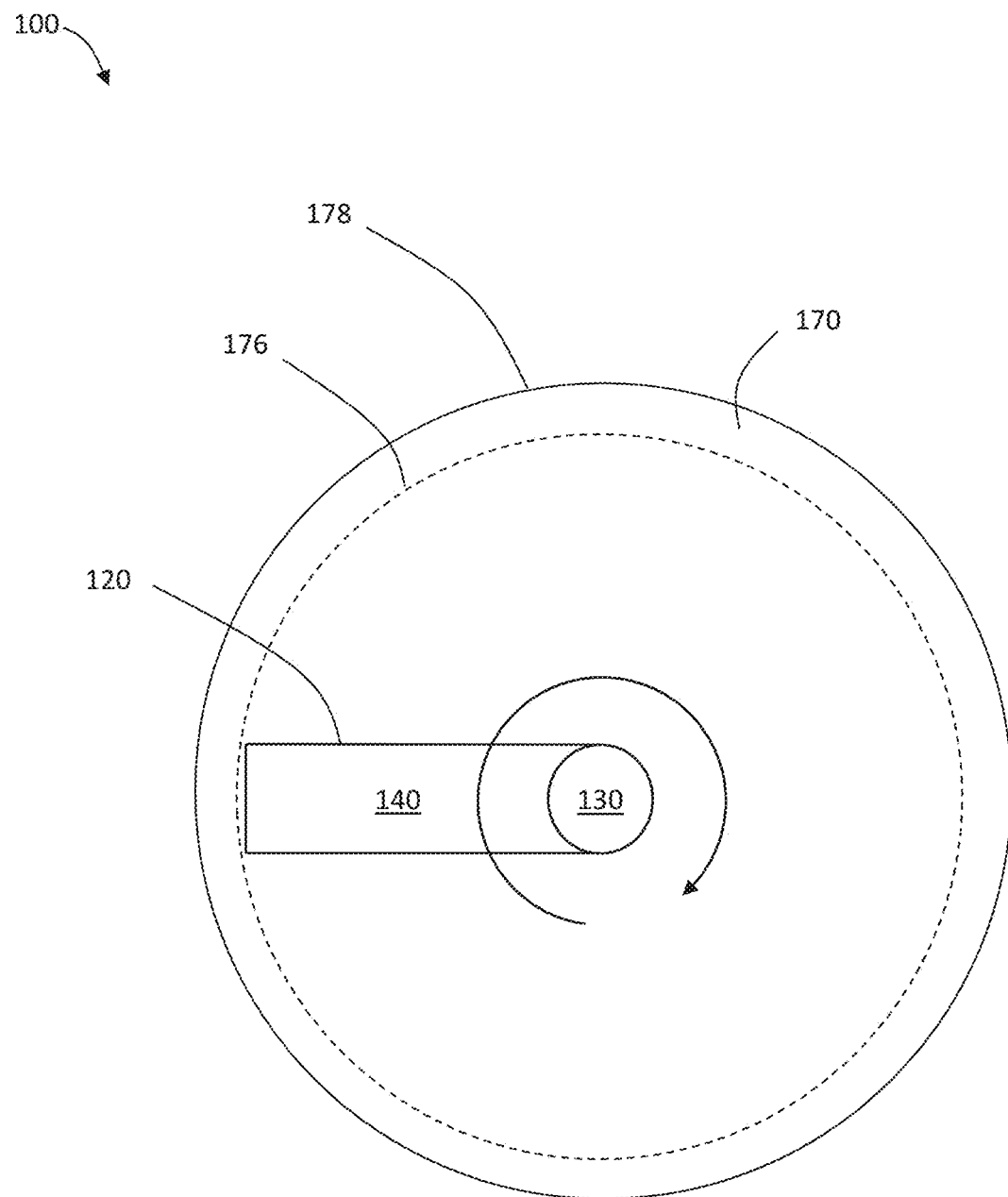
FIG. 1D is a top view schematic illustration of a filtration device comprising a fin extending in one direction, according to one set of embodiments.
Figure 1E:
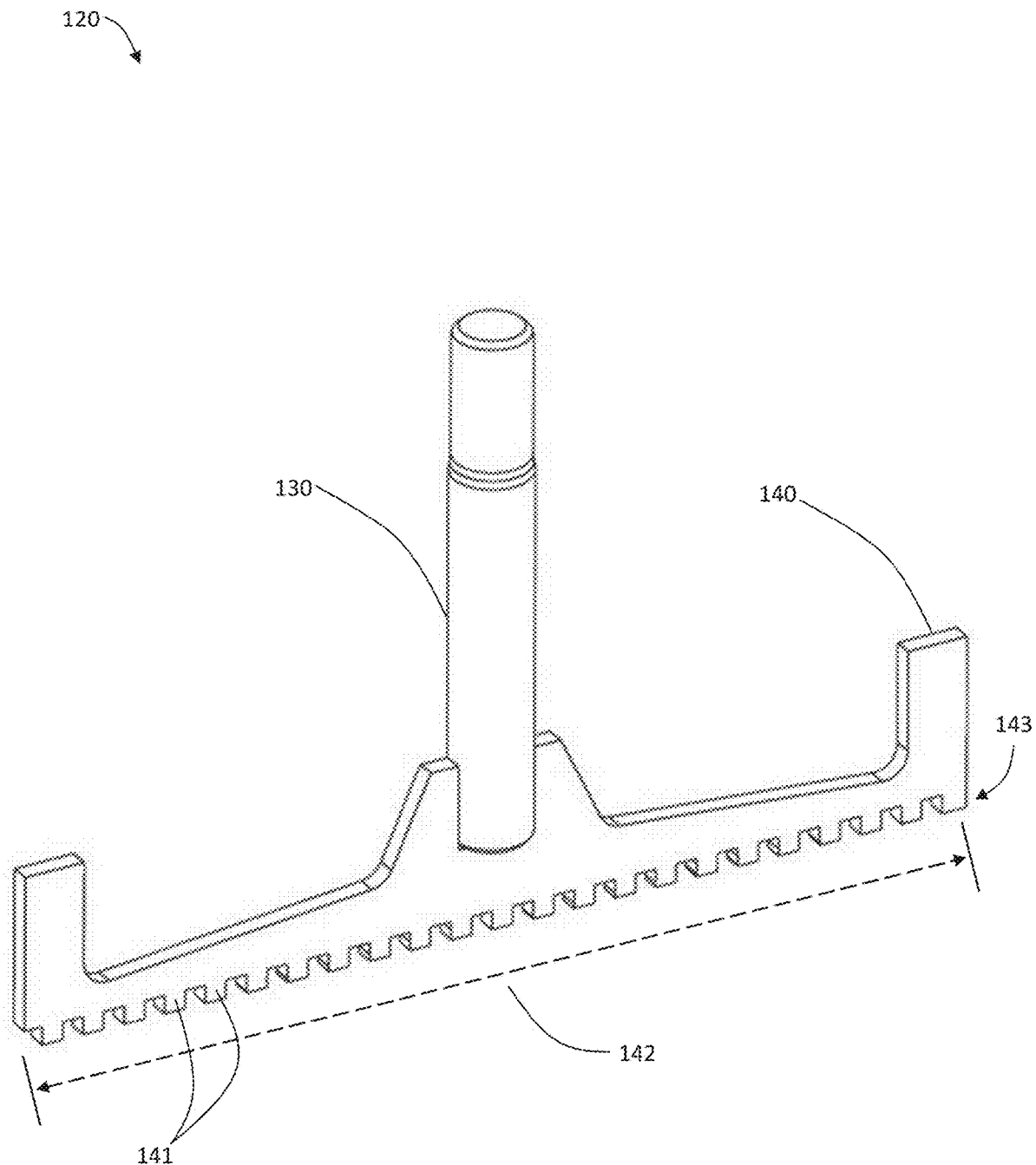
FIG. 1E is a perspective view schematic illustration of an impeller of a filtration device, in accordance with certain embodiments.
Figure 1F:
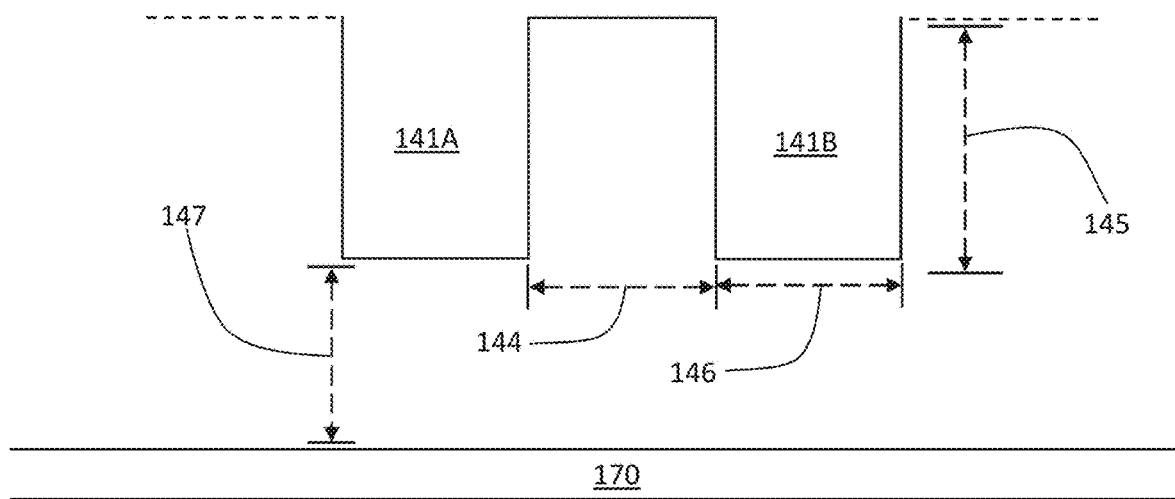
FIG. 1F is a schematic illustration a plurality of protrusions of a fin, according to certain embodiments.
Figure 1G:
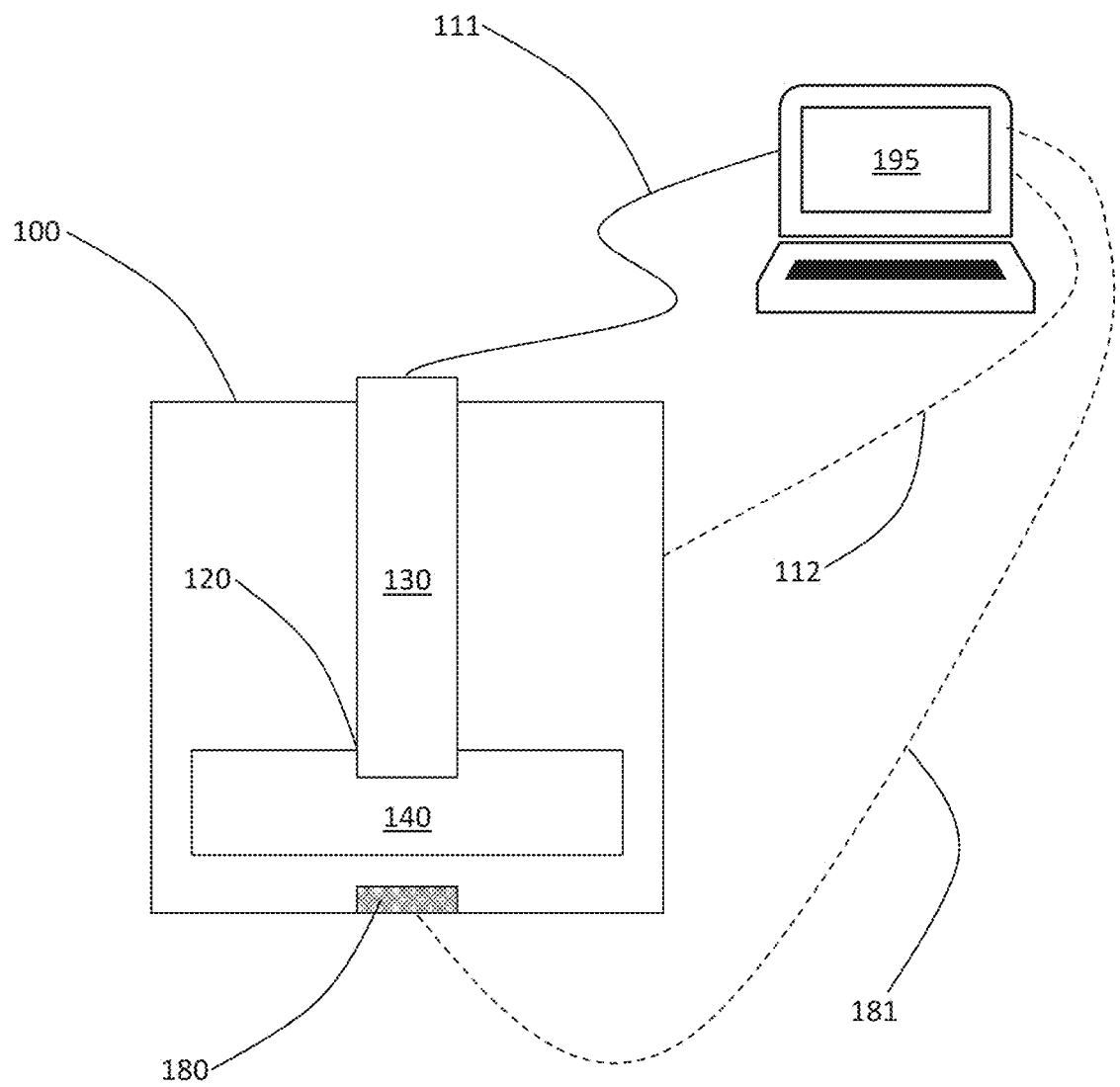
FIG. 1G is a schematic illustration of a controller connected to a filtration device, according to one set of embodiments.
Figure 1H:
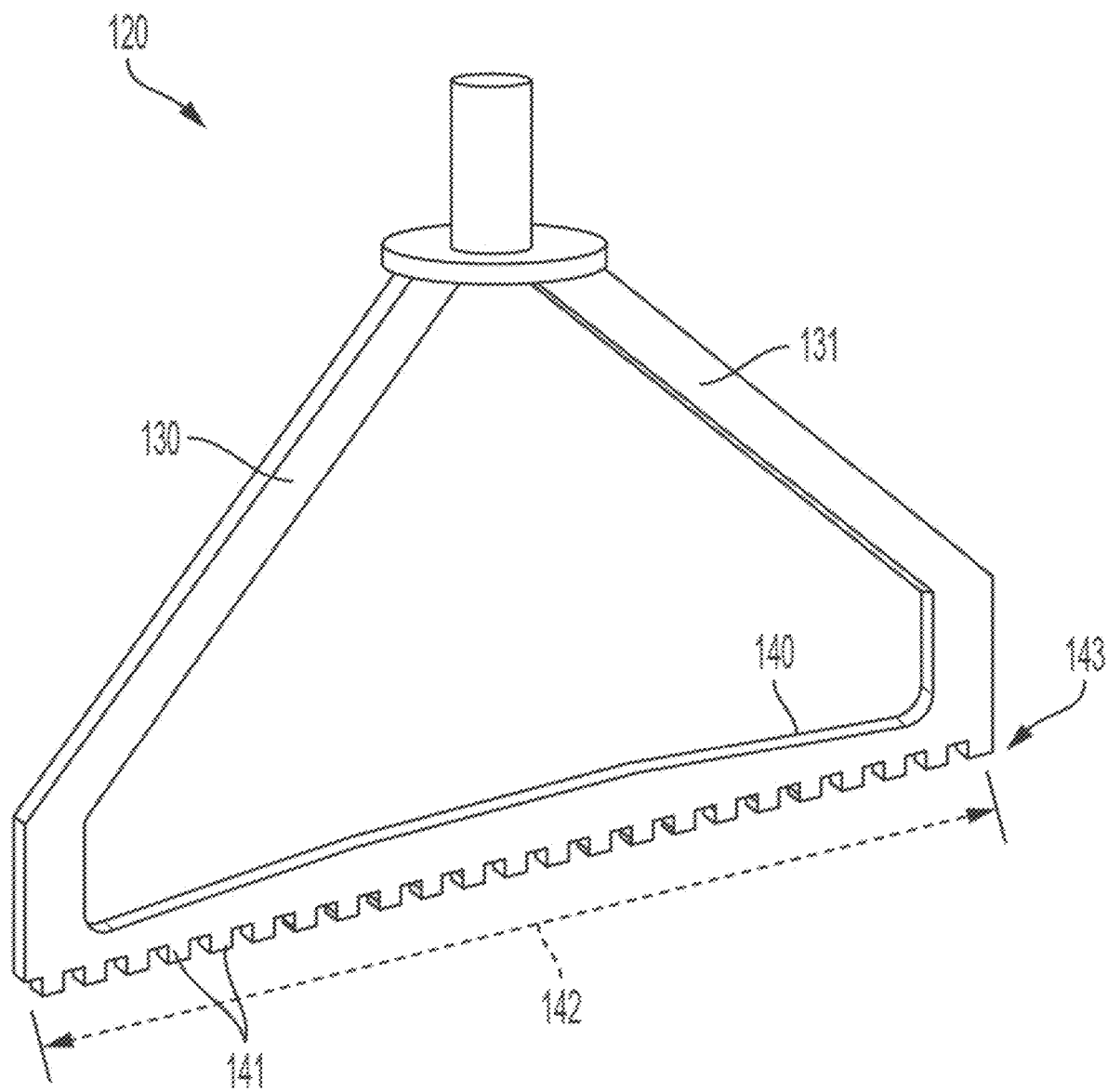
FIG. 1H is a perspective view schematic illustration of an impeller comprising a plurality of shafts attached to a single fin, in accordance with certain embodiments.

In certain embodiments, the filtration device comprises a rotating edge comprising a plurality of protrusions extending from the edge toward the filtration medium. The edge can be, for example, part of an impeller. One example of such a configuration is illustrated in FIG. 1A, where filtration device 100 comprises impeller 120. The impeller comprises, in some embodiments, a shaft and at least one fin. For example, in FIGS. 1A, 1C-1E, and 1G, impeller 120 comprises shaft 130 and fin 140. While fin 140 is illustrated in FIGS. 1A, 1C, and 1E-1G as extending in two opposite directions from shaft 130, other configurations could also be used. As a non-limiting example, FIG. 1D is a schematic showing fin 140 extending in one direction from shaft 130. Generally, the term "fin" is used herein to refer to an elongated body that extends from a shaft. The "fin" can extend in a single direction, in some embodiments, as shown in FIG. 1D. The "fin" could also extend in two directions that are opposite from each other, as shown in FIGS. 1A, 1C, and 1E-1G. Yet another example is shown in FIG. 1H, in which a single fin 140 extends from both of shaft 130 and shaft 131.

In certain embodiments, more than one, more than two, or more than three fins may be present. In some embodiments, and as described in more detail below, the fin(s) of the impeller may sweep the facial surface of the filtration medium when the shaft of the impeller is rotated.

The edge that sweeps the filtration medium may also comprise a plurality of protrusions, according to certain embodiments. For example, in some embodiments, the fin(s) of the impeller may include a plurality of protrusions that sweep the filtration medium when the impeller is rotated. These protrusions may advantageously break up solid particles too large in particle size and may also delump agglomerates or aggregates of solid particles (such as a solid API). In some embodiments, rotating the edge (e.g., by rotating the impeller) promotes breakage of millimeter scale agglomerates (e.g., agglomerates having maximum cross-sectional dimensions of between 100 micrometers and 10 millimeters) comprising the active pharmaceutical ingredient. Agglomerates and/or aggregates of solid particles (e.g., solid particles of an API) may comprise particles that are bound together, and delumping of agglomerates and/or aggregates of solid particles by the fin may promote breaking of these bound particles into smaller, unbound particles. In some embodiments, the edge comprises at least 5 protrusions (or at least 10 protrusions, or at least 20 protrusions) spaced periodically along the edge facing the filtration medium. For example, in FIG. 1E, fin 140 comprises 23 protrusions along edge 143, which face the filtration medium after assembly. Similarly, in FIG. 1H, edge 143 comprises 23 protrusions which face the filtration medium after assembly.

The edge may be configured to mix or agitate a solid or a suspension prior to, during, or after filtration via rotation of the edge (e.g., via rotation of a shaft of an impeller into which the edge is integrated). FIG. 1E is a schematic illustration of an impeller, which may be used in certain embodiments of the filtration devices and methods described herein. In FIG. 1E, impeller 120 comprises shaft 130 and fin 140. The shaft may rotate impeller (and at least one fin) thereby providing motion to agitate a suspension or slurry comprising a solid API. Furthermore, fin 140 comprises a plurality of protrusions 141. When arranged in the filtration device, such as filtration device 100, the protrusions of the impeller may extend toward the filtration medium, such as filtration medium 170 shown in FIG. 1A. FIG. 1E also shows a schematic of a lateral axis 142 along the fin 140. FIG. 1H is a schematic illustration of another exemplary impeller, which may be used in certain embodiments of the filtration devices and methods described herein. In FIG. 1H, impeller 120 comprises shaft 130, shaft 131, and fin 140. Shafts 130 and 131 may be rotated, thereby providing motion to agitate a suspension or slurry comprising a solid API. Fin 140 further comprises a plurality of protrusions 141 which, when arranged in the filtration device, may extend toward the filtration medium, such as filtration medium 170 shown in FIG. 1A.

As noted above, an impeller may comprise one or more shafts for providing motion to the impeller. The shaft(s) may be attached to an external device (such as a motor, as non-limiting example) to provide such motion.

In some cases, it can be advantageous to use an impeller comprising a shaft and fin(s), with the edge comprising the protrusions arranged along the fin(s). For example, such designs can be easy to clean, and they may be relative easy to actuate. It should be understood, however, that the invention is not necessarily limited to the use of filtration systems comprising impellers with a shaft and one or more fins, and in other embodiments, the shaft and fin(s) arrangement is not required. As one example, a magnetically coupled blade comprising protrusions could be used, in some embodiments. Those of ordinary skill in the art, provided with the present disclosure, would be capable of designing alternative configurations that can be used to achieve the relative motion between the edge comprising the protrusions and the filtration medium.

In some embodiments, the edge comprising the protrusions is rotatable in both a clockwise direction and a counterclockwise direction. That is to say, in certain embodiments, the edge is capable of being rotated in both a clockwise and a counterclockwise direction. In certain embodiments, the edge is configured to rotate in both a clockwise and a counterclockwise direction during use. For example, in some embodiments, a controller connected to the impeller can be programmed to rotate the shaft in both a clockwise and a counterclockwise direction during use. In some cases, it may be advantageous to rotate the shaft a clockwise direction, subsequently rotate the shaft a counterclockwise direction, and then subsequently rotate the shaft in a clockwise direction. In some embodiments this can be repeated relatively quickly (e.g., before completing more than 10, more than 5, or more than 2 rotations in each direction). In accordance with some embodiments, a rotational direction of the impeller changes at least once (or at least two times, at least five times, at least 10 times, at least 100 times, or more) during the rotating. In some embodiments, the rotational speed of the edge is at least 5 revolutions per minute (RPM), at least 10 RPM, at least 30 RPM, or at least 60 RPM during each rotation segment (i.e., during each of the periods of time between the change in rotation direction). In some embodiments, the direction of rotation can be changed at least 2 times per minute, at least 5 times per minute, at least 10 times per minute, at least 60 times per minute, at least 120 times per minute, or more. Rotating the impeller in multiple directions in relatively quick succession can be useful, in some cases, in breaking up lumps and/or individual crystals containing API, which can result in the production of relatively consistently-sized API crystals and/or particles. In some embodiments, rotation of the impeller by the shaft causes the at least one fin to sweep the filtration medium.

As noted above, the filtration device may comprise an edge comprising one or more protrusions, the rotation of which can be used to help agitate a liquid, solid particles, or a suspension of the two. Not wishing to be bound by any particular theory, it is believed that the distance from the edge to the filtration medium may impact the particle size of solid particles retained by the filtration medium. The distance from the edge to the filtration medium can be measured as the shortest distance from a protrusion along a lateral axis of the edge to the facial area of the filtration medium. According to some embodiments, the shortest distance between the edge and the filtration medium is 1 mm or less. For example, in FIG. 1F, the shortest distance between edge 143 and filtration medium 170 is indicated as distance 147, which can be 1 mm or less, in certain embodiments. In some embodiments, a distance between the edge and the filtration medium controls a particle size of the active pharmaceutical ingredient.

In some embodiments, the plurality of protrusions on the one or more edge(s) may be of a certain dimension (e.g., lateral dimension, protruding dimension, average spacing, etc.) and/or spacing relative to the filtration medium to promote crystal breakage and/or delumping.

According to certain embodiments, the protrusions from the edge can be spaced periodically. The spacing between adjacent protrusions refers to the shortest distance between the adjacent protrusions. For example, in FIG. 1F, the spacing between protrusion 141A and 141B corresponds to distance 144. A plurality of protrusions are considered to be spaced "periodically" when distributions of the spacings between adjacent protrusions within the plurality is such that no single spacing deviates by more than 25% from the number average of the spacings. In some embodiments, periodically spaced protrusions are spaced such that no single spacing deviates by more than 10%, by more than 5%, or by more than 2% from the number average of the spacings. Protrusions that are spaced periodically may advantageously help control the particle size of an API. It should be understood, however, that non-periodically spaced protrusions could also be used.

The protrusions may have, in some embodiments, a particular spacing. In some embodiments, the average spacing between the plurality of protrusions on the edge is at least 1 mm. In some embodiments, the average spacing between the plurality of protrusions on the edge is from 1 mm to 1 cm. Such spacings may, in some embodiments, aid in the breakup of agglomerates and/or crystals containing an API. It should be understood that the use of such spacings is not required, and in other embodiments, other spacings may be used.

Use of protrusions having particular protruding dimensions can be beneficial, in some embodiments. As used herein a "protruding dimension" of a protrusion refers to the dimension of the protrusion that is perpendicular to the edge from which it protrudes. For example, in FIG. 1F, protrusion 141B comprises protruding dimension 145. The protruding dimension may advantageously assist in breaking up large particles or agglomerates of API as to produce an API of a desired particle size. In some embodiments, at least a portion (or all) of the plurality of protrusions have a protruding dimension of at least 1 mm, at least 2 mm, at least 5 mm, or more. In certain embodiments, at least a portion (or all) of the plurality of protrusions have a protruding dimension of up to 10 mm, up to 2 cm, or more. Combinations of these ranges are also possible. Other ranges are also possible.

Use of protrusions having particular lateral dimensions can also be beneficial, in some embodiments. As used herein a "lateral dimension" of a protrusion refers to the dimension of the protrusion that is parallel to the edge from which it protrudes. For example, in FIG. 1F, protrusion 141B comprises lateral dimension 146. In some embodiments, at least a portion (or all) of the plurality of protrusions have a lateral dimension of at least 1 mm, at least 2 mm, at least 5 mm, or more. In certain embodiments, at least a portion (or all) of the plurality of protrusions have a lateral dimension of up to 10 mm, up to 2 cm, or more. Combinations of these ranges are also possible. Other ranges are also possible.

In some embodiments, movement and/or rotation of the edge may be controlled by a controller. The controller may receive an input from another component of a filtration device, such as from a temperature sensor (e.g., a thermocouple) or heating region, and adjust the rotational motion of the edge comprising the protrusions (e.g., by adjusting the rotational motion of the associated impeller). FIG. 1G is a schematic illustration of a system in which filtration device 100 is connected to controller 195. In FIG. 1G, controller 195 is connected by electronic coupling 111 (e.g., a wired or wireless connection) to impeller 120. Controller 195 may also be optionally coupled to the filtration device and/or to a temperature sensor of the filtration device.

In some embodiments, the controller is configured to receive a signal from the temperature sensor and adjust a rotational configuration of the edge. It may be beneficial to provide a certain rotational configuration once a suspension comprising solid API particles is at a desired temperature. By way of example and not limitation, the controller may adjust a rotational configuration from clockwise to counterclockwise once the temperature sensor receives a signal from the temperature sensor that this threshold temperature has been reached. As another non-limiting example, the controller may be configured to change a rotational configuration (e.g., from counterclockwise to clockwise) when the controller receives a signal from the temperature sensor that the temperature has reached a certain minimum temperature.

In some embodiments, the controller is configured to receive a signal from the temperature sensor and adjust a speed of the edge comprising the protrusions based, at least in part, on the signal received from the temperature sensor. In some cases, the temperature sensor may detect a certain temperature threshold and the controller may receive this data and increase or the speed of rotation of the edge (e.g., by adjusting the rotational speed of the shaft(s) that are part of the impeller that includes the edge).

In some embodiments, adjusting a speed of rotation of the edge is based, at least in part, on a temperature of at least one component of the filtration device.

In some cases, heating may be provided, either separately or in tandem with rotation of the edge. In some such embodiments, a heating region may be present within the filtration device. The heating region may be located proximate the filtration medium and/or the edge comprising the protrusions. In some embodiments, the heating region is located between the filtration medium and the edge comprising the protrusions. In some embodiments, the heating element may be positioned below the filtration medium. Other positions for the heating region are also possible. The heating region may comprise a heater or a heating element. Any device that provides heat may be used including, but not limited to, resistive heaters and inductive heaters. In some embodiments, it can be beneficial to use an inductive heater, as such use can provide heat directly to the suspension, the liquid, and/or the solid particles. In some cases, providing heat to the solid particles may advantageously control the crystallization of the solid particles. In some instances, it may be desired to provide heat to slow or prevent crystallization of solid particles such that the flowability remains high, which may facilitate further processing, such as forming the solid particles into a tablet.

Providing heat to at least a portion of the filtration device may, in accordance with certain embodiments, assist in filtering a suspension and/or in determining the particle size or crystallinity of the solid particles. In some embodiments, the heat provided is controlled, at least in part, by a controller. Additionally, heating may work in communication or in tandem with the control of the edge speed or direction (e.g., using the controller). In FIG. 1G, for example, controller 195 is connected to impeller 120 via electronic coupling 111. The controller is also optionally connected to temperature sensor 180 and filtration device 100 via connections 112 and 181 respectively. Through connections 112 and 181, the heating may be adjusted and the motion or rotation of the edge comprising the protrusions may also be adjusted based of a signal from temperature sensor 180 through controller 195.

As noted above, in some embodiments, the filtration device may include a temperature sensor. Any of a variety of temperature sensors can be employed, such as a thermocouple, a resistance temperature detector (RTD), a semiconductor-based temperature sensor, a negative temperature coefficient (NTC) thermistor, and the like. In some embodiments, the temperature of the at least one component (such as a heating region proximate filtration medium and/or the impeller) may be measured by the temperature sensor. The temperature sensor may be connected to a heating element, such as an inductive heating plate, in order to directly control the temperature of the heating element. In some embodiments, the temperature sensor is connected to a controller wherein the controller is also connected to a heating element, such that the controller may control the temperature. In certain embodiments, the controller is configured to receive a signal from the temperature sensor and adjust a heating level of the heater based, at least in part, on the signal received from the temperature sensor. The temperature sensor may also communicate with the edge comprising the protrusions, either directly or through the controller. In certain cases, adjusting a speed of rotation of the edge is based, at least in part, on a temperature of at least one component of the filtration device.

In some cases, it may be beneficial to provide or remove gas from a chamber within a filtration device or according to methods described herein. Accordingly, a filtration device may be equipped with a gas inlet port, such as gas inlet port 160 in FIG. 1A. Appropriate tubing (such as Tygon™ tubing) or any suitable connection may be attached to the gas inlet port to establish a connection with a vacuum source (e.g., a vacuum pump) and/or to a gas source (e.g., a compressed air source). Any of a variety of external gases may be applied, such as nitrogen, argon, and helium. Conversely, a vacuum may be applied to remove gas from a filtration device. Application of a vacuum may assist in drying the API by removing residual solvent and other volatile compounds that may remain. In some embodiments, isolating an API of a desired particle size involves establishing a vacuum in the space through which the edge sweeps the filtration medium (e.g., the space between the impeller and the filtration medium) during at least a portion of the rotating of the edge comprising the protrusions. The pressure (i.e., the amount of gas or the amount of vacuum applied) may be monitored externally by a pressure or vacuum gauge. In some cases, isolating the API (such as drying the API) may involve flowing compressed air through a gas inlet port and across an API.

According to certain embodiments, it may be desirable to provide additional solvent to a suspension or to wash an API with additional solvents. This may be accomplished, in some embodiments, with a filtration device equipped with a solvent port, such as solvent port 150 in FIG. 1A. Any solvent suitable for washing an API may be used, in accordance with certain embodiments, such as hexanes, diethyl ether, toluene, dichloromethane, ethyl acetate, isopropyl alcohol, ethanol, methanol, and water, as non-limiting examples. It should be noted that as used herein, a "solvent" refers to a liquid that can dissolve a substance; however, in some cases the API may or may not be soluble in a given solvent. In many cases, the API is not soluble in a solvent, such that the solvent may be used to wash or remove impurities (i.e., undesired chemical species) from an API. Those of ordinary skill in the art will be capable of selecting an appropriate solvent for isolating and washing an API.

It should be appreciated that while a solid API may be isolated using devices and methods described herein, some embodiments may also be used to remove an unwanted solid from a liquid comprising an chemical species to be isolated. The slurry may be passed through the filtration medium and the liquid comprising the chemical species collected, while the unwanted solid remains in the filtration device on top of the filtration medium.

Devices and methods described herein may be used to isolate an active pharmaceutical ingredient, or an API. In some embodiments, the API has an elongated crystalline structure. For example, in some embodiments, the API comprises Ciprofloxacin Hydrochloride. In some embodiments, the API comprises melitracen hydrochloride, salicylic acid, acetaminophen, and/or aliskiren hemifumarate.

According to some embodiments, the API may be one or a combination of therapeutic, diagnostic, and/or enhancement agents, such as drugs, and tracers. In some embodiments, the API is a nutraceutical, prophylactic or diagnostic agent. While much of the specification describe isolating an active pharmaceutical ingredient, other ingredients are also possible. Ingredients may include, but are not limited to, any synthetic or naturally-occurring biologically active compound or composition of matter which, when administered to a subject (e.g., a human or nonhuman animal), induces a desired pharmacologic, immunogenic, and/or physiologic effect by local and/or systemic action. For example, useful or potentially useful within the context of certain embodiments are compounds or chemicals traditionally regarded as drugs, vaccines, and/or biopharmaceuticals. Certain such APIs may include molecules such as proteins, peptides, hormones, nucleic acids, gene constructs, etc., for use in therapeutic, diagnostic, and/or enhancement areas, including, but not limited to medical or veterinary treatment, prevention, diagnosis, and/or mitigation of disease or illness (e.g., HMG co-A reductase inhibitors (statins) like rosuvastatin, nonsteroidal anti-inflammatory drugs like meloxicam, selective serotonin reuptake inhibitors like escitalopram, blood thinning agents like clopidogrel, steroids like prednisone, antipsychotics like aripiprazole and risperidone, analgesics like buprenorphine, antagonists like naloxone, montelukast, and memantine, cardiac glycosides like digoxin, alpha blockers like tamsulosin, cholesterol absorption inhibitors like ezetimibe, metabolites like colchicine, antihistamines like loratadine and cetirizine, opioids like loperamide, proton-pump inhibitors like omeprazole, anti(retro) viral agents like entecavir, dolutegravir, rilpivirine, and cabotegravir, antibiotics like doxycycline, ciprofloxacin, and azithromycin, anti-malarial agents, and synthroid/levothyroxine); substance abuse treatment (e.g., methadone and varenicline); family planning (e.g., hormonal contraception); performance enhancement (e.g., stimulants like caffeine); and nutrition and supplements (e.g., protein, folic acid, calcium, iodine, iron, zinc, thiamine, niacin, vitamin C, vitamin D, and other vitamin or mineral supplements). Other APIs are also possible.

Figure 11A:
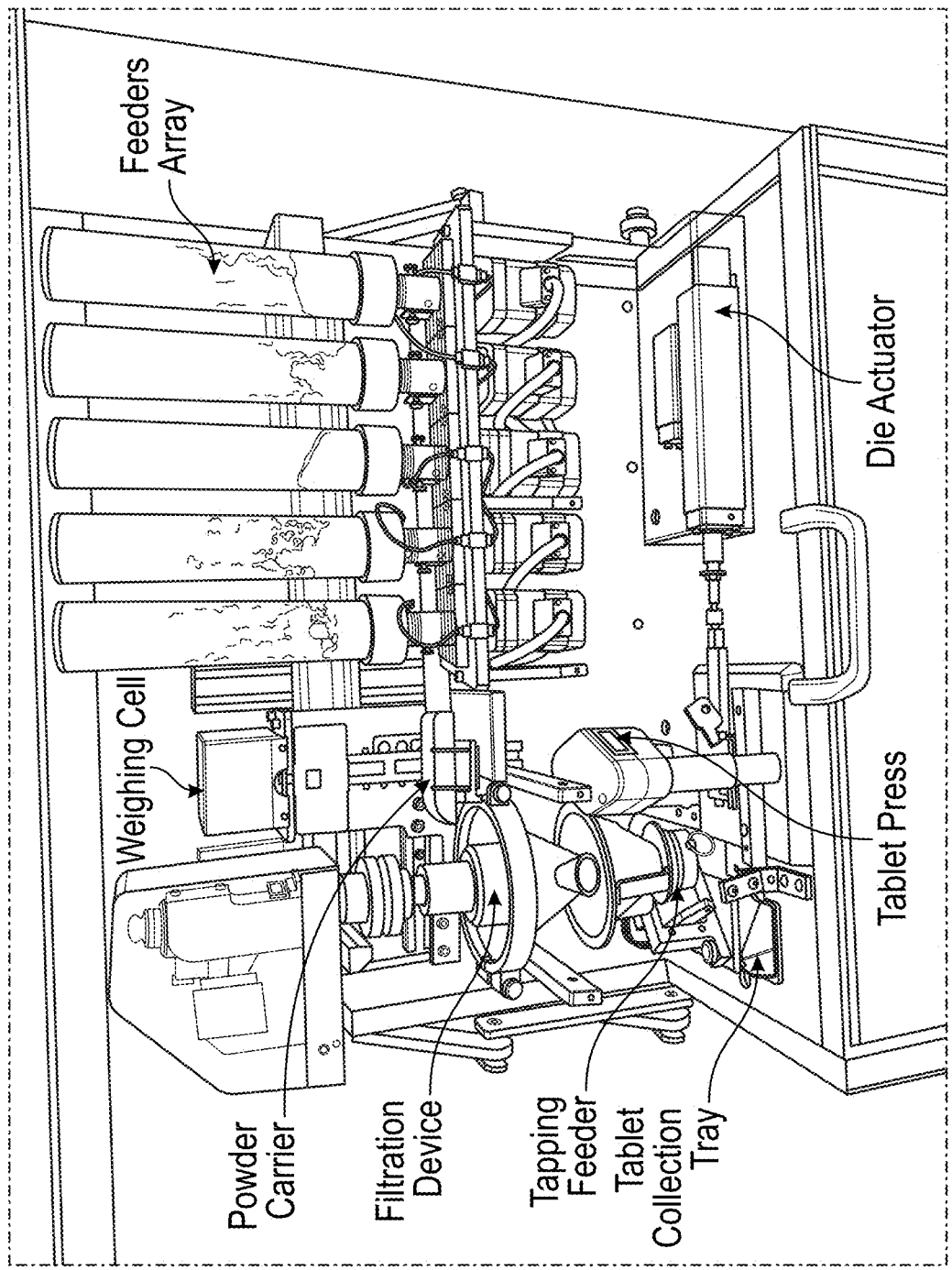
FIGS. 11A-11B show a drawing and a schematic of a compact, portable, re-configurable, and automated tablet manufacturing unit incorporating a filtration device, in accordance with certain embodiments.
Figure 11B:
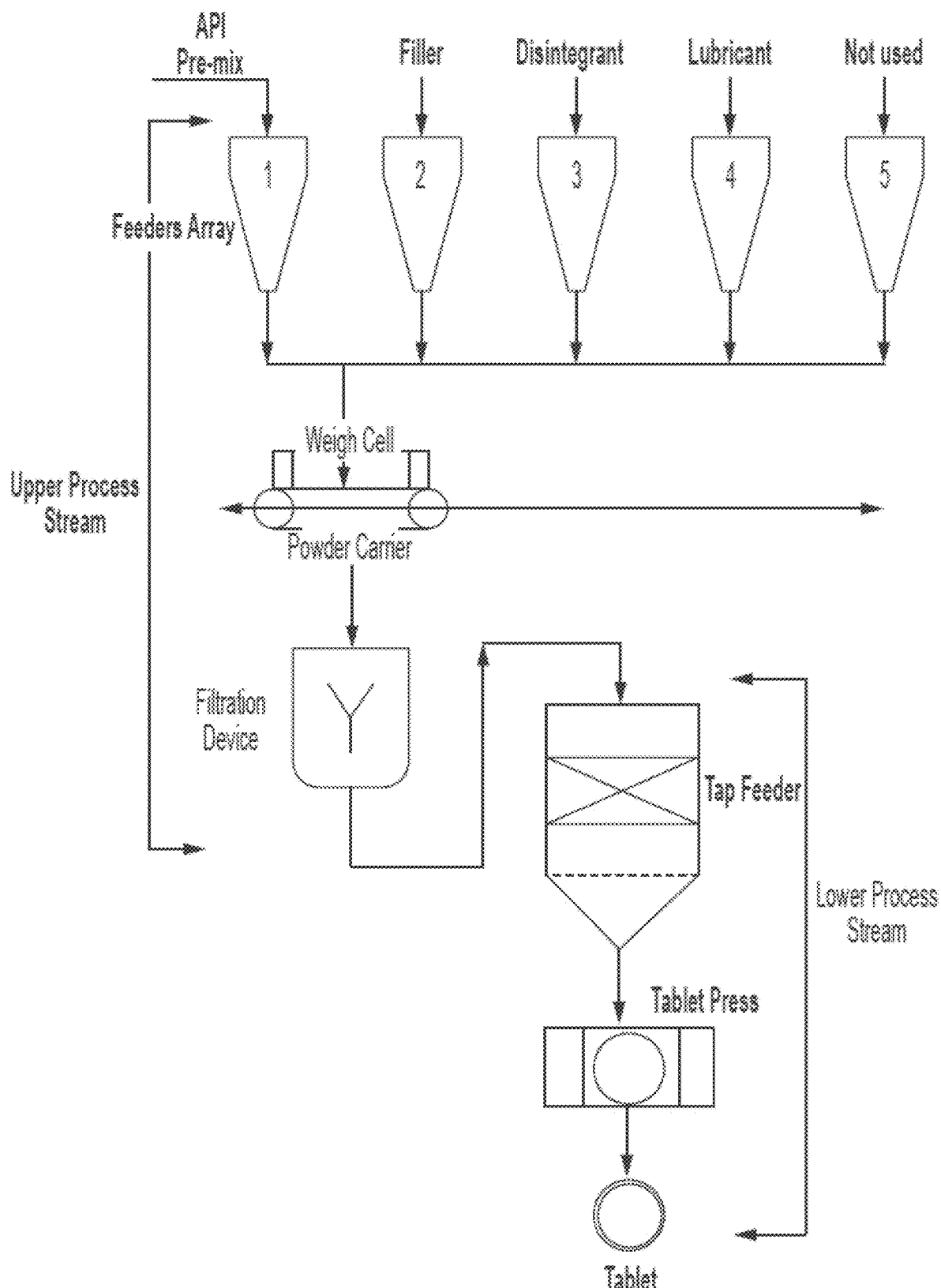

In certain embodiments, the filtration device may stand-alone as a device, functioning independently from other devices. In some embodiments, the filtration device may be part of another device, apparatus, or a part in a manufacturing process, as devices and methods described herein may advantageously be used in a "plug-and-play" manner, denoting or relating to devices that are intended to function when used or connected to another device without reconfiguration or adjustment. A non-limiting example of a filtration device incorporated into another device is described in at least Example 2 of this disclosure and is seen in FIGS. 11A-11B. In some embodiments, the filtration device can be incorporated into a crystallizer.

U.S. Provisional Application No. 62/903,571, filed Sep. 20, 2019, and entitled "Devices and Methods for the Integrated Filtration, Drying, and Mechanical Processing of Active Pharmaceutical Ingredients" and U.S. Provisional Application No. 62/904,240, filed Sep. 23, 2019, and entitled "Devices and Methods for the Integrated Filtration, Drying, and Mechanical Processing of Active Pharmaceutical Ingredients" are each incorporated herein by reference in their entirety for all purposes.

The following examples are intended to illustrate certain embodiments of the present invention, but do not exemplify the full scope of the invention.

Example 1

This example describes the filtration, drying, and delumping of a suspension comprising Ciprofloxacin using a filtration device.

Ciprofloxacin hydrochloride (99.8% purity) was purchased from Jai Radhe and used as the model API. Formic acid (≥95% purity) was purchased from Sigma-Aldrich. Isopropanol (≥99.5% purity) and acetone (≥99.5% purity) were purchased from VWR Chemicals.

Figure 14A:
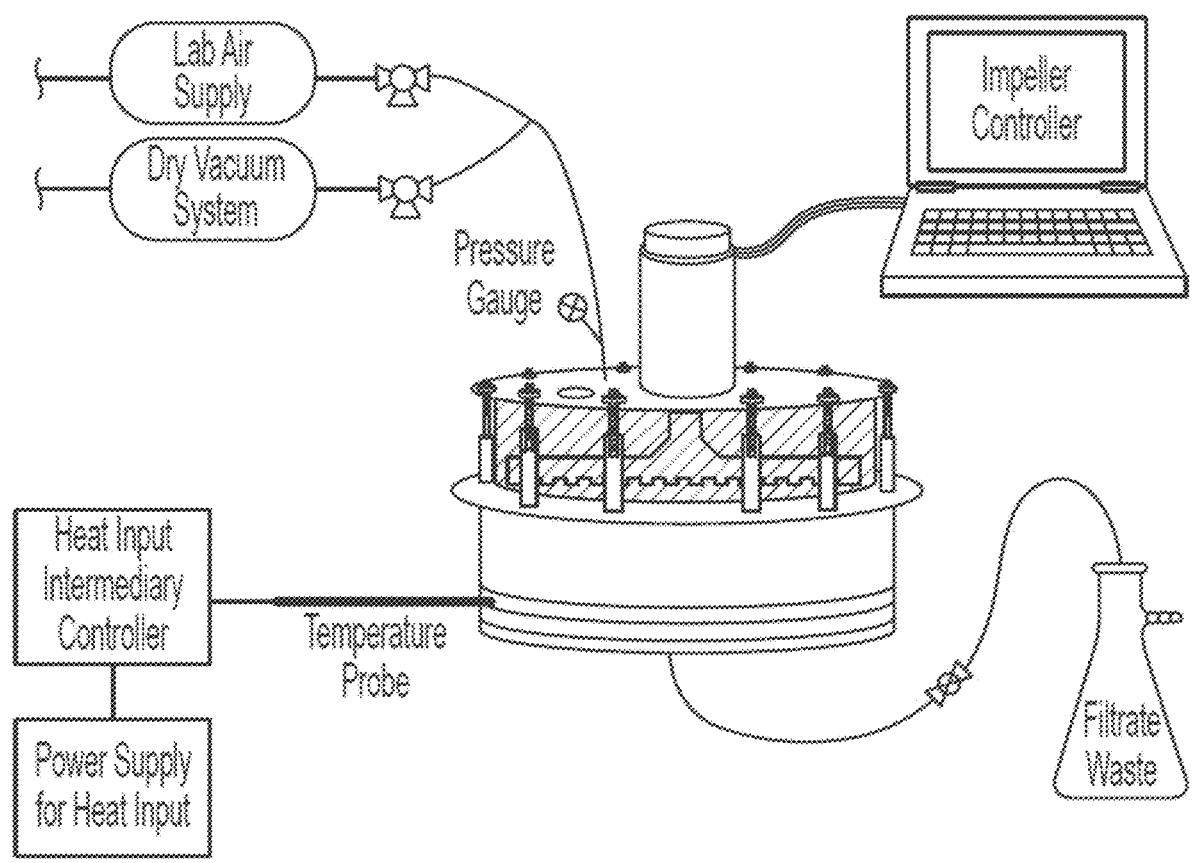
FIGS. 14A-14B shows a schematic of an exemplary grinder/impeller and a drawing of the exemplary grinder/impeller, according to one set of embodiments.
Figure 14B:
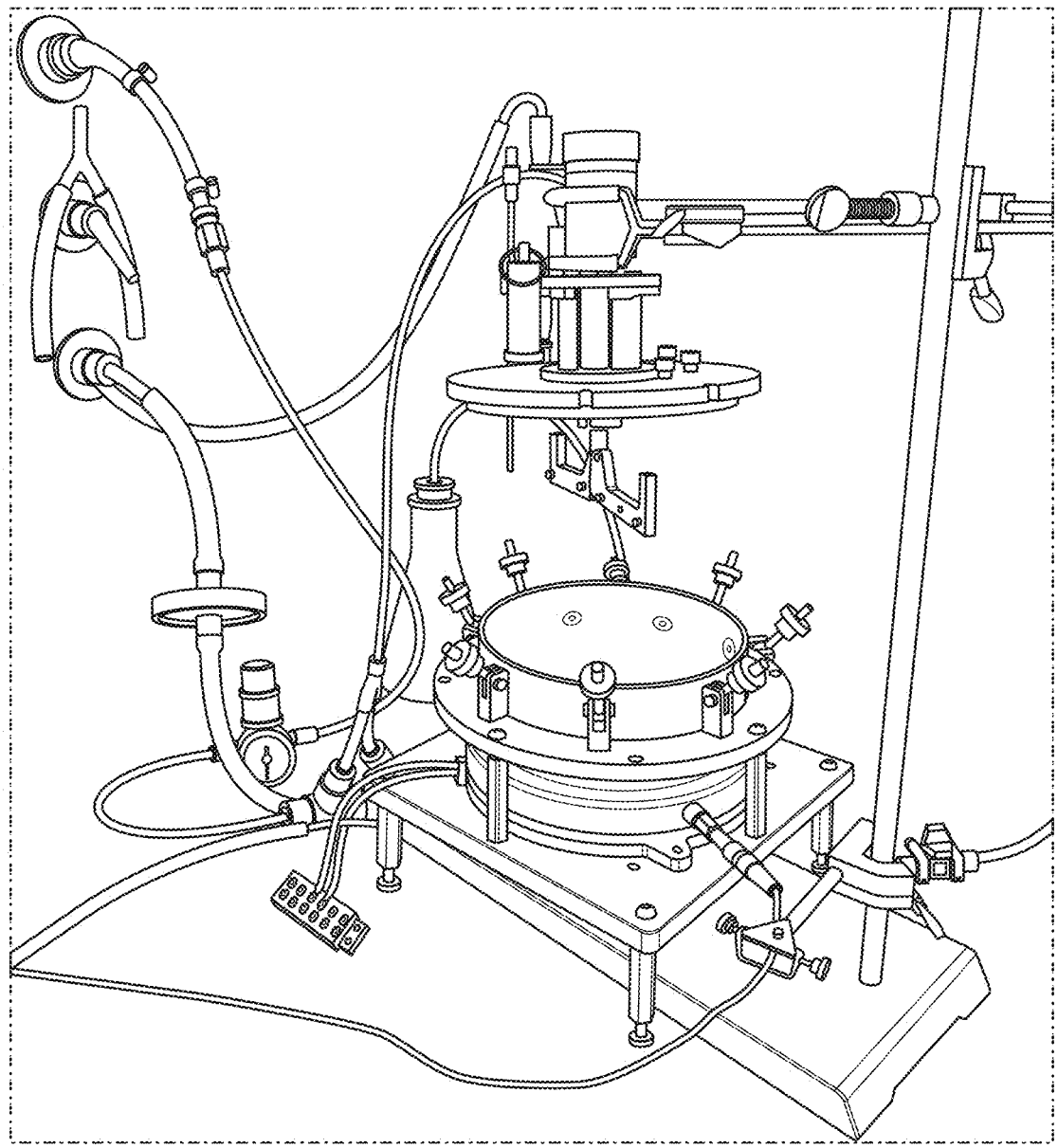

The filtration device is illustrated in FIG. 14B. The filtration device used in this example benefitted from the implementation of a specific impeller design and a set of feedback control systems to integrate several unit operations into a single piece of equipment.

The overall dimensions of the device were 200 mm length×200 mm width×260 mm height, with the main compartment having a 1300 mL capacity. The body of the vessel and the impeller were built of C-276 Hastelloy steel. The vessel lid is built in aluminum 6061 and coated with perfluoroalkoxy copolymer resin (PFA) on the product side. Furthermore, the lid includes a ⅜" port for suspension transfer, four ⅛" ports to feed wash solvents, two ¼" pressure/vacuum ports, a 2 barg pressure release valve and a 25 mm glass observation window. The impeller is connected to a Maxon motor EC 45 with a Planetary Gearhead GP 42 C.

The impeller fin promoted the breakage of mm-scale soft lumps and μm-scale elongated crystals. Lump breakage was promoted by means of a plurality of protrusions (each protrusion having the dimensions of 3.5 mm width×3 mm height×3.1 mm thickness) that allowed the fine powder pass through while retaining the larger lumps. Whether those lumps break or simply rotate depends on their dry matter content, with dry lumps presenting tightly bound particles. With the appropriate in situ assessment of the drying process, the dry matter content of the drying powder was assessed in real time to ensure that agitation was applied at the right time during the drying step. Breakage of single crystals was promoted from the distance between the impeller fins and the filter mesh, adjusted at approximately 0.5 mm. For a free flowing bulk powder, crystals larger than this dimension will break upon being dragged by the moving fin.

The filter mesh can be heated by means of an induction heating plate located at the base. The inductive heater was connected to a temperature controller, from which isothermal conditions were maintained during drying operation. In contrast to other heating methods involving the use of a jacketed filter or passing heating fluid through the impeller, directing the heat to the filter plate via the inductive heater allowed for a more even heat distribution throughout the filter mesh and minimized temperature spikes that could promote dehydration or degradation of heat-sensitive compounds.

The filtration device was connected to the laboratory compressed air and vacuum supplies. A manometer was connected to monitor the filtration and drying pressures. Furthermore, the filtration pressure was controlled through a reduction valve connected to the compressed air supply. The inductive heater was connected to a house-made temperature controller. Instead of providing an adjustable heating power, the controller maintained a fixed wattage, and the percentage of time by which electrical power was supplied to the inductive heater was controlled instead. Heating was thus provided in cycles of 2 seconds in duration, during which power was supplied for a user-defined percentage of time, and no power was supplied for the remaining time. With this approach, the heat duty to maintain isothermal conditions was accurately tracked in real time via the heating frequency.

To test the filtration device, a suspension containing elongated Ciprofloxacin hydrochloride monohydrate crystals was generated via continuous Mixed Suspension Mixed Product Removal (MSMPR) crystallization. This compound presents two major challenges for the filtration process. First, it tends to crystallize as needle-like particles, leading to a poor flowability and compressibility during the formulation steps. Second, USP specifications for this drug substance specify a lattice water content between 4.7% and 6.7%. This range corresponds roughly to the monohydrate form of the API. It is thus desirable for the drying and delumping processes to break the needle-like crystals and efficiently remove the bulk water without dehydrating the API.

MSMPR crystallization experiments were conducted in a 2000 mL round bottom jacketed vessel (ID=130 mm), equipped with a 60 mm pitched-fin 45° down-pumping propeller operating at 250 rpm. The operating volume was set to 800 mL, with an average residence time of 2 hours and a crystallization temperature of 5° C. Feed transfer, antisolvent transfer, and product withdrawal were conducted via programmable peristaltic pumps (Masterflex P/S with Easy-Load II pump heads) using ¼" Masterflex PharmaPure tubing. The operating volume was controlled by a dip pipe, and setting the product withdrawal pump to the maximum flow rate (87 mL/min).

The feed solution for crystallization was prepared containing 100 mg/mL of commercial API in 1:4 formic acid: water. The experiment started as a fed-batch crystallizer, by which antisolvent was pumped at 5.3 mL/min to 160 mL of feed solution. In this process, isopropanol was used as antisolvent. To ensure that the monohydrate form of Ciprofloxacin HCl is obtained, 0.5 g of commercial API was added as seeds to the fed-batch crystallizer when the solvent: antisolvent ratio was approximately 1:2. The antisolvent addition was completed when the solvent:antisolvent ratio reached 1:4. For these ratios, the resulting solvent composition is 4 vol. % formic acid, 16 vol. % water, 80 vol. % isopropanol. At this point, continuous transfer of feed and antisolvent was started at 1.33 mL/min and 5.33 mL/min, respectively. The MSMPR experiment was then continued for 24 hours, collecting 10 liters of API suspension on each crystallization experiment. The suspension density, typically between 17 mg/mL and 18 mg/mL, was verified by filtration of a 50 mL sample followed by oven drying of the wet cake at 50° C. for three days.

The API suspension, pre-cooled to 5° C., was filtered at 15 psig. Solid loadings of 18 g and 35 g were studied, corresponding to 1000 mL and 2000 mL of suspension volume, respectively. Immediately after filtration, a sample of the wet cake was collected for analysis under X-Ray Powder Diffraction (XRPD). This sample was taken to verify that the monohydrate form of the API was being fed to the filtration device.

The filtered cake was washed using 4:1 acetone:water with a ratio of 4.6 mL/g API. The use of 20 vol. % water in the wash solvent was necessary to prevent dehydration of the API. The solids were suspended in the wash solvent for 2 minutes, stirring at 30 rpm with an impeller direction switch every 30 seconds. Then, agitation was stopped and the wash solvent was deliquored at 15 psig. Two samples of approximately 0.5 g were collected from the washed cake. The first was used for crystal structure verification under XRPD, for determination of the water content by Karl Fischer (KF) analysis, and for crystal shape determination under optical microscopy. The second sample was weighed and placed in the oven at 50° C. for three days to assess the dry matter content. To ensure that the samples were representative of the bulk cake, they were taken from the vertical cross-section of the wet cake, accounting for any possible variations in dry matter along the axis perpendicular to the filter plate.

Drying of the washed cake was conducted at 50° C. and 0.5 bar (absolute pressure) for variable drying times between 60 min and 140 min. Early experiments showed dehydration of the API at 85° C. and 0.5 bar (absolute pressure). The temperature was thus kept at 50° C. to provide a sufficient buffer for possible temperature and pressure fluctuations. Furthermore, early experiments revealed that agitating from the start of the drying process leads to the attachment of the wet cake on top of the impeller fins, drying as a single lump. Consequently, the first 20-40 min of the drying process were conducted in static mode. Determining the end of the static drying step was challenging, as the drying times are highly dependent on the starting dry matter content and the solids load.

At the end of the static drying step, an agitation program was activated, by which the impeller would rotate at 30 rpm with a direction switch every 30 seconds. This step is referred to as the delumping process. The drying powder tended to follow the rotating impeller, forming a dune in front of the fin. A sudden direction switch leads to the destabilization of this dune, and its subsequent breakage by the fin moving in the opposite direction. This ultimately promotes bulk powder mixing, homogeneous drying, and an even delumping of the cake.

Analogous to the sampling methods during the washing step, two 0.5 g samples were taken approximately every 20 minutes during the drying process. The first was used for XRPD, KF and image analysis. The second was used to determine the dry matter content in the drying cake. Loss on drying was measured after leaving the sample in the oven at 50° C. for three days. Additional XRPD analysis was conducted to verify that the samples did not dehydrate in the oven.

At the end of the drying process, the powder was collected and sieved at 500 μm to calculate the fraction of delumped material. Then, the particle size distribution of the sieved powder was determined by laser diffraction.

XRPD patterns of the solid cake were obtained for 2θ between 5° and 40° using a PANalytical X'Pert Pro MPD diffractometer equipped with a reflection/transmission spinner stage. Karl Fischer analysis was conducted using a Metrohm 831 KF Coulometer. The API samples were dissolved in dry dimethylsulfoxide, and the water contents were corrected by the results on pure solvent. Optical microscopy pictures of the powder were obtained using a Nikon Eclipse ME600 optical microscope equipped with a Nikon DS-Ri1 camera. Particle size analysis by laser diffraction was conducted in a Malvern Mastersizer 2000 using a Scirocco 2000 dry dispersion unit. The refractive index for the API was set to 1.66.

Figure 2:
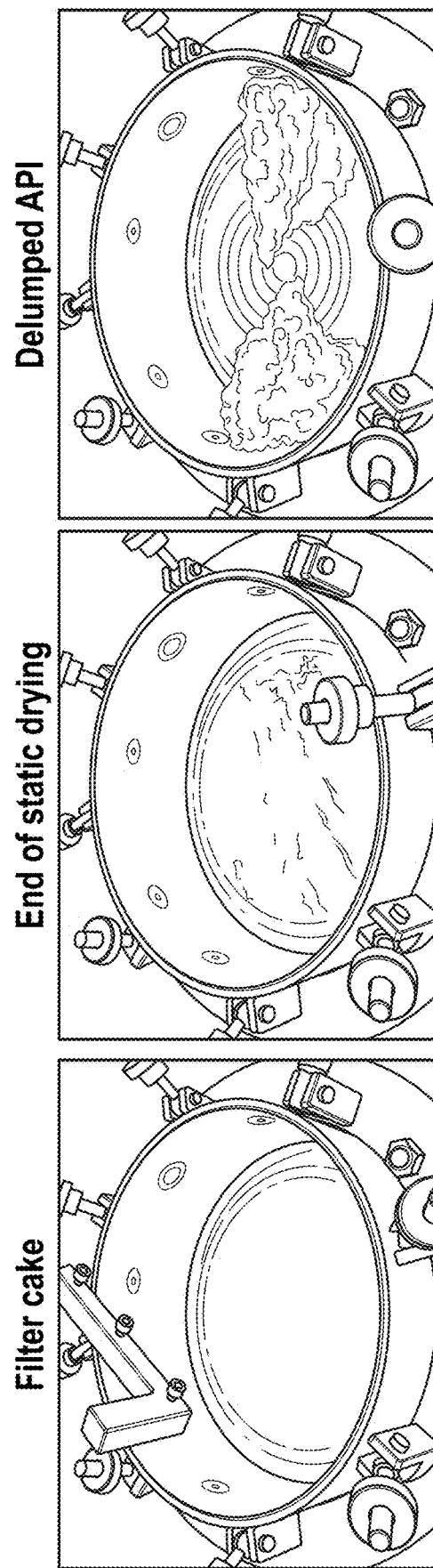
FIG. 2 is a series of drawings showing the appearance of an API cake at different points during a process, according to some embodiments.

Example 1 was conducted with a solids load of 28 g, obtained from the filtration of 1600 mL of API suspension. The objective was to characterize the effects of drying time on API hydration, dry matter content, fraction of lumped API, crystal aspect ratio, and particle size distribution. The drying step was maintained for a total of 140 min, from which the first 20 min were sustained without agitation, and the latter 120 min were operated with impeller rotation of 30 rpm and direction switch every 30 seconds. The appearance of the solid cake at different steps during the process is illustrated in FIG. 2.

Figure 3:
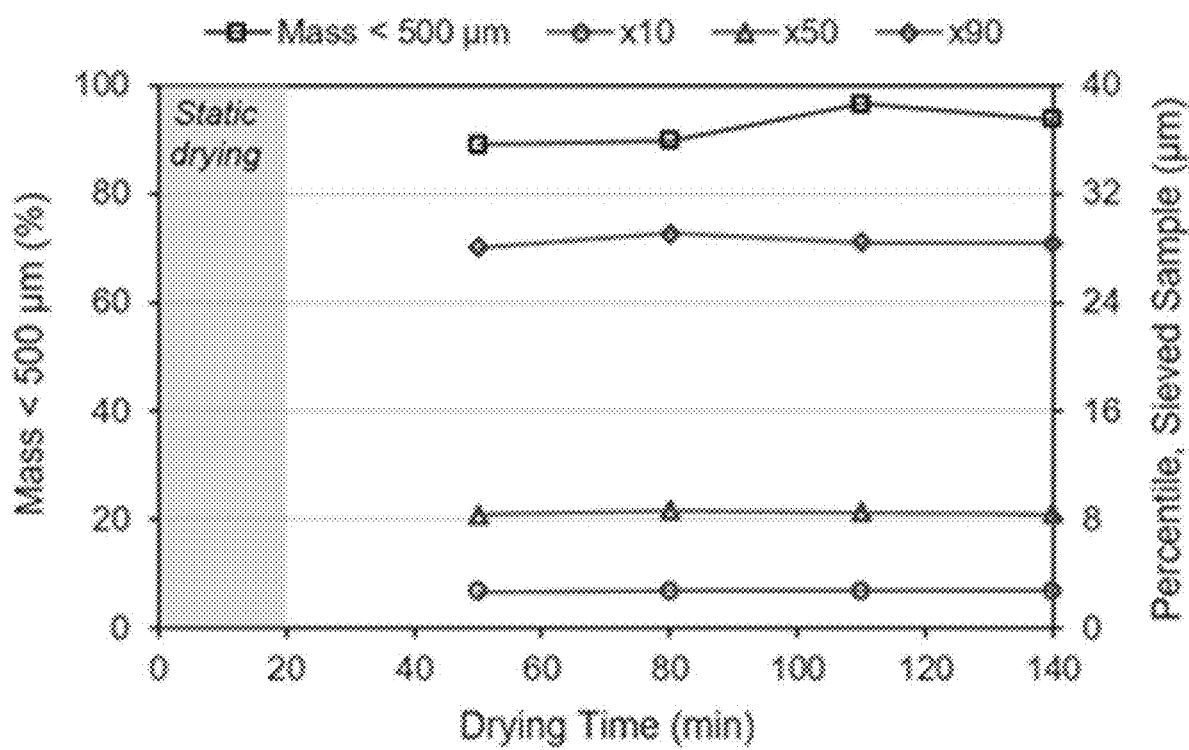
FIG. 3 shows a fraction of delumped material passing through a 500 μm sieve and resulting particle size distribution percentiles from laser diffraction, according to one set of embodiments.
Figure 4A:
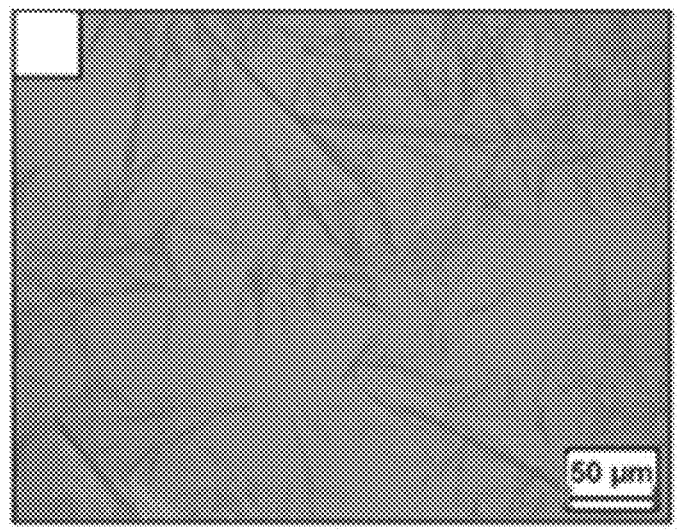
FIGS. 4A-4E show optical microscopy images of APIs after various delumping times, according to certain embodiments.
Figure 4B:
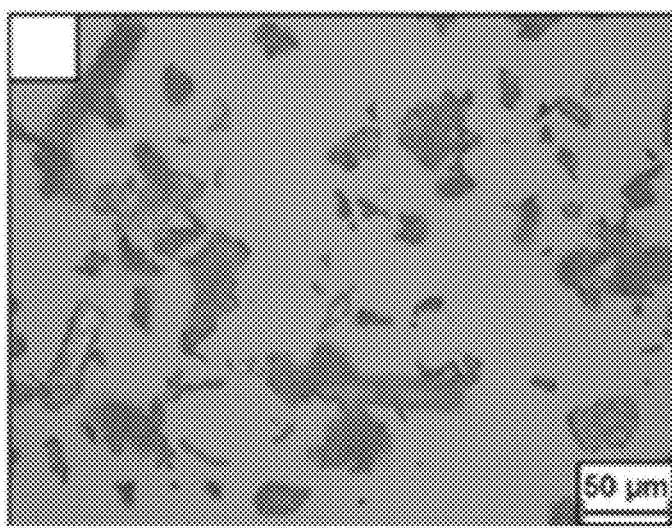
Figure 4C:
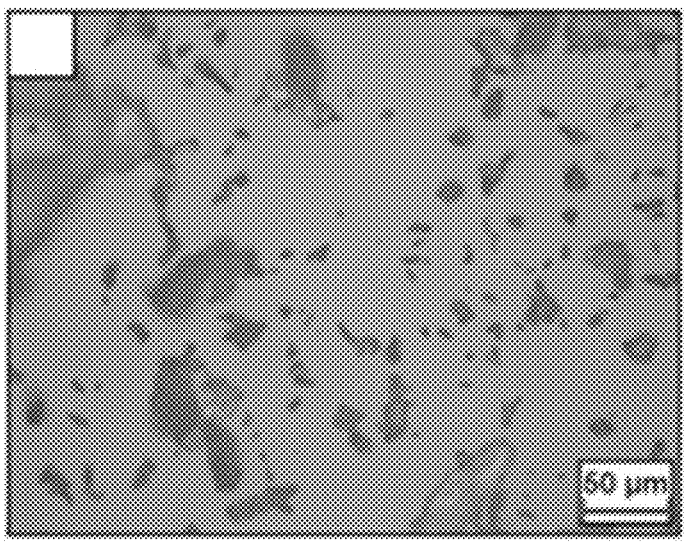
Figure 4D:
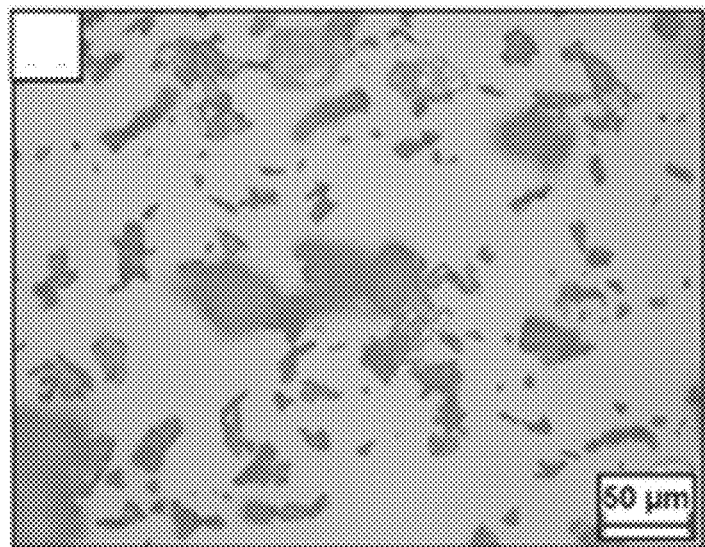
Figure 4E:
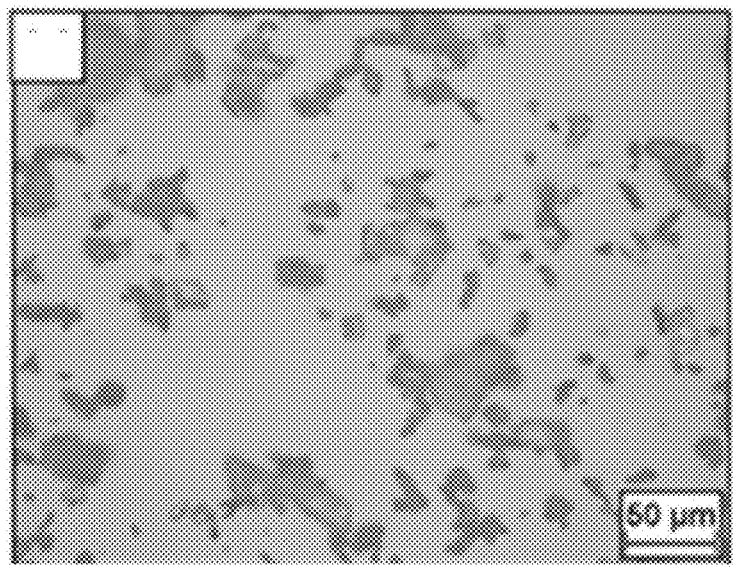

In this example, 30 minutes of agitated drying were sufficient to fully delump the drug substance. This can be observed in FIG. 2, and it was verified quantitatively from the sieving yield loss at different drying times. The appearance of the API cake at different points during the process. Static drying was maintained for 20 min at 50° C., 0.5 bar (absolute pressure). The API was delumped after 30 min of agitation. To obtain representative samples, 1.5 g of material were removed for each sample. These were sieved at 500 μm and then analyzed by laser diffraction. FIG. 3 shows the mass fraction of powder passing a 500 μm sieve for different drying times, together with the particle size distribution percentiles from laser diffraction. The fraction of delumped material passing through a 500 μm sieve and resulting particle size distribution percentiles from laser diffraction supported these different drying times.

Results from this experiment show that, for a 28 g solids load, 30 min of agitation might be enough to reach the maximum delumping yield. A similar effect was observed for the particle size distribution control. Because the starting material was a suspension, and the solid API is part of a single lump at the end of static drying, it was not possible to measure the particle size distribution using the same dry dispersion method. As an alternative approach, optical microscopy pictures were taken of the starting suspension, as well as from the powder at different stages of the drying process. The obtained results, seen in FIG. 4, verify a significant reduction of crystal aspect ratio and particle size. FIG. 4 shows optical microscopy images of the API (a) after crystallization, (b) after 30 min of delumping, (c) after 60 min of delumping, (d) after 90 min of delumping, (e) and after 120 min of delumping.

Since the laser diffraction results can be affected by variations in crystal aspect ratio, the combined imaging (FIG. 4) and laser diffraction data (FIG. 3) support that both the particle shape and particle size remained constant throughout the agitation process. Variations in the stirring speed and in the impeller blade location could contribute to an improved particle size control.

Since the laser diffraction results was affected by variations in crystal aspect ratio, the combined imaging (FIG. 4) and laser diffraction data (FIG. 3) supported that both the particle shape and particle size remained constant throughout the agitation process. This is to be expected for elongated crystals, as their fragility is highly dependent on the aspect ratio. With needle-like crystals being relatively easy to break along the width axis, the ease of breakage should decrease as the aspect ratio becomes smaller. At some point, it is expected that most crystal dimensions will be significantly smaller than the spacing between the filter plate and the impeller fin. Variations in the stirring speed and in the impeller fin location could contribute to an improved particle size control.

Figure 5:
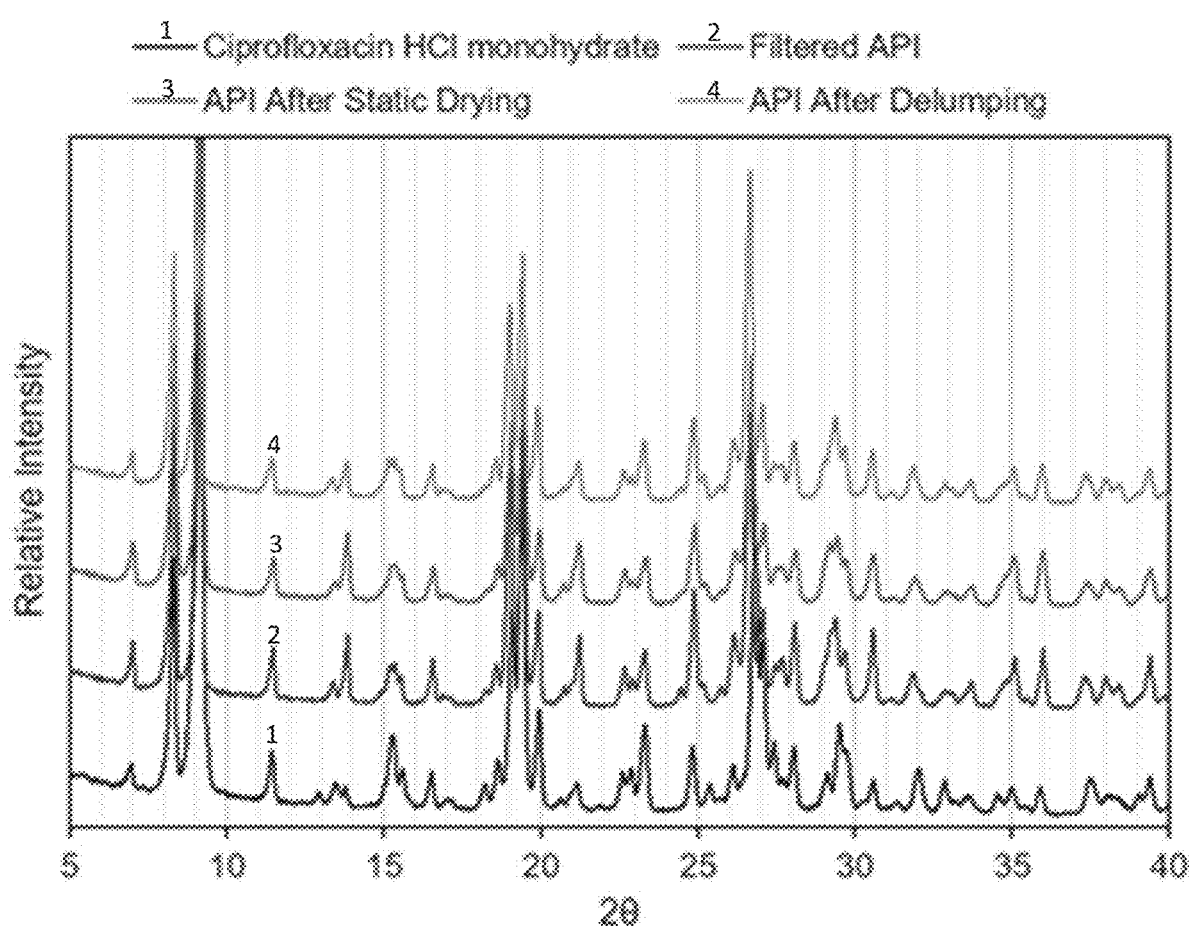
FIG. 5 shows x-ray powder diffraction patterns of API at the end of filtration, static drying, and delumping steps, compared to commercial Ciprofloxacin HCl monohydrate, according to one set of embodiments.

Another important aspect of this process was the isolation of the monohydrate form of ciprofloxacin HCl, with lattice water contents between 4.7 and 6.7% to meet USP specifications. The drying and delumping processes was thus intense enough to dry and delump the powder within reasonable processing times, but mild enough to prevent API dehydration or loss of crystallinity. The XRPD patterns of the drug substance at different points of the process are reported in FIG. 5.

Figure 6:
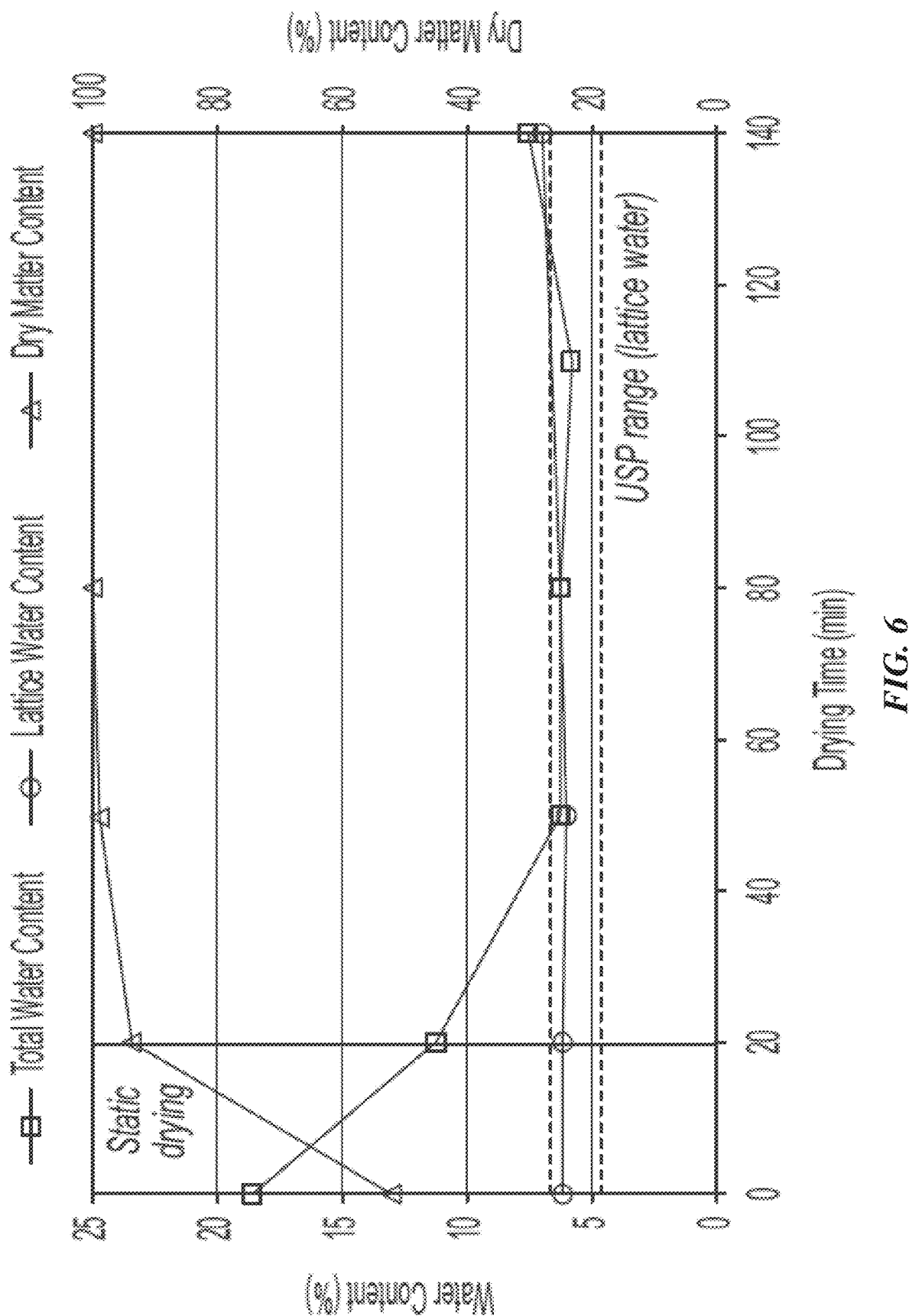
FIG. 6 shows dry matter, bulk water, and lattice water mass fraction trends for an API cake during a drying process, according to one set of embodiments.

XRPD analysis of the recovered powder revealed that, even after 140 min of drying, the API retained the original crystal structure. Furthermore, no significant loss of crystallinity can be observed from the baseline. The lattice water content can be quantified from KF analysis of the off-line oven dried samples collected at different times during the process. In FIG. 6, these results have been compared with the cake dry matter content and water content measured before oven drying. As expected, the cake contains approximately 19 wt % water at the start of the drying process, coming from the residual wash solvent that contains 20 vol % water (24 wt %), but diluted by the solid API. The lattice water contents obtained from KF analysis show that the crystalline phase contained 6.2 wt % of lattice water. This value is in accordance with the observations from XRPD analysis, with the monohydrate salt of ciprofloxacin HCl having a 4.7 wt % stoichiometric water content. As the drying step progresses, the total water concentration in the cake decreases while the lattice water is maintained constant. With the USP specifications giving a target water content between 4.7 and 6.7 wt %, the obtained drug substance started meeting the specifications after 50 min of drying. This time coincides with the point at which the cake dry matter content was near 100%.

Overall, results from this experiment show that the process can deliver dry ciprofloxacin HCl monohydrate powder within 60 min of drying time. Additional drying and delumping times, although unnecessary, do not pose a risk for the stability of the crystal structure or the particle size distribution. With the appropriate selection of drying conditions (temperature and pressure) and mixing speed, this device can consistently deliver the desired crystal quality attributes in a reasonable processing time.

Figure 7:
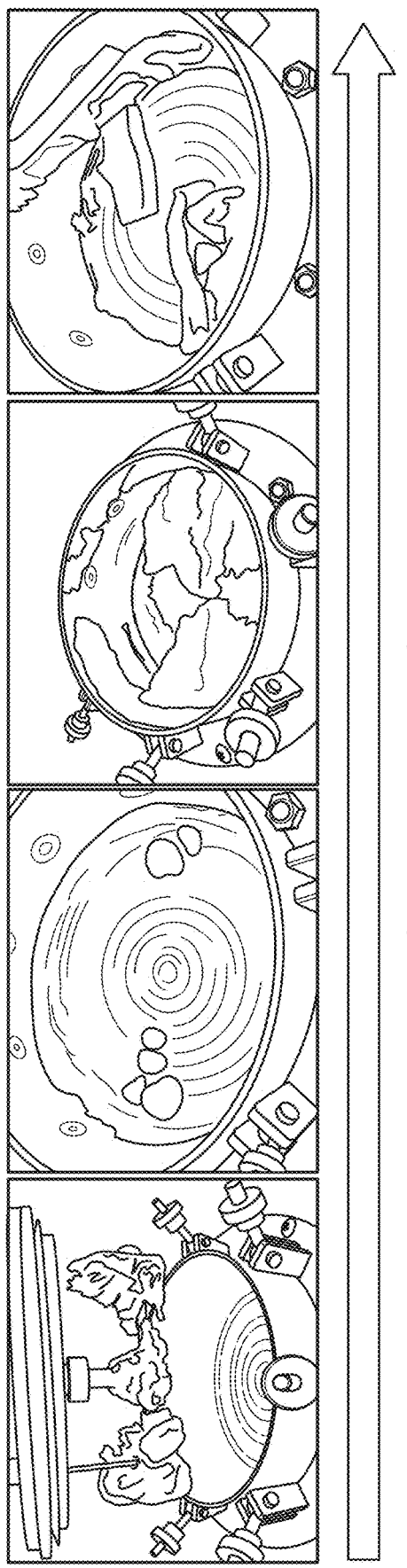
FIG. 7 shows an end product of a drying step depending on the starting dry matter content of the cake, according to some embodiments.

To evaluate the reproducibility of the drying process, and to optimize the solids load to maximize yield and productivity, a set of experiments were conducted at increased solids loads of 35 g and 70 g. While the drying temperature and pressure were kept constant at 50° C. and 0.5 bar, the duration of the static drying step was increased to compensate for higher API loads. The delumping time was kept constant at 60 min. Depending on the dry matter content of the cake at the start of delumping, the process yielded fine powder, a lump of cake attached to the impeller, or cake that is too cohesive to be broken by the limited torque of the motor. Examples of these scenarios have been illustrated in FIG. 7.

There is, usually, an optimal range of dry matter content at which the cake is dry enough to detach from the impeller during the direction switch, but not too dry that it cannot be processed by the motor. Note that the higher end of this range is heavily affected by the cake thickness and it could be expanded by use of a stronger motor. However, because this device was designed for use in portable modules, there amount of suitable motors with higher torque is limited.

Table 1 below summarizes the drying conditions for seven experiments at different solid loads and static drying times. Note that the dry matter content at the end of the washing step, once the wash solvent is deliquored, can vary significantly between experiments that share similar loads and deliquoring times. In runs 6 and 7, the deliquoring times were increased substantially to allow for approximately 120 seconds of drying from the compressed air flow. This scenario could easily be encountered in a manufacturing environment, where the system would be programmed with a constant deliquoring time, but variations in the filtration rate (e.g., by cake resistance or pressure fluctuations) could lead to significantly different dry matter contents.

TABLE 1

Summary of experimental conditions for the experiments at variable API loads and deliquoring times. The end product appearance is assessed after 60 min of delumping, unless the cake cannot be broken by the impeller (hard cake).

| Run | API load (g) | Deliquoring time (s) | DM after deliquoring (%) | Static Drying (min) | DM before delumping (%) | End product |
|---|---|---|---|---|---|---|
| 1 | 28 | 23 | 52.2 | 20 | 93.6 | Free powder |
| 2 | 35 | 60 | 41.8 | 40 | 77.5 | Free powder |
| 3 | 35 | 45 | 58.8 | 40 | 74.7 | Free powder |
| 4 | 35 | 50 | 46.0 | 40 | 79.9 | Free powder |
| 5 | 70 | 55 | 27.3 | 70 | 54.0 | Attached to the impeller |
| 6 | 70 | 180 | 62.6 | 70 | 93.1 | Hard cake |
| 7 | 70 | 210 | 66.4 | 40 | 94.4 | Hard cake |

Especially when the heat is supplied directly to the filter plate, thicker cakes can lead to significant dispersion in dry matter content along the vertical axis. This behavior could explain why, despite having significantly different static drying times, runs 6 and 7 led to a very similar dry matter content at the end of static drying. A gradient in solvent content for high solid loads will eventually lead to the formation of unprocessable hard cake at the bottom of the plate, and a layer of wet cake at the top that would attach to the impeller. The optimal range of dry matter contents at which delumping can be started was thus limited by the solids load. This narrow range could explain the results obtained with API loads of 70 g.

In an automated process environment, where API loads and deliquoring times are hard to control, and drying times can heavily depend on the equipment sealing, temperature fluctuations, and pressure fluctuations, a large number of failed drying cycles could be expected if the drying times are set to a predetermined value. Development of a control strategy to assess the cake dry matter content in situ was thus critical to ensure consistent product quality and account for variable drying times. In this context, a strategy was developed by which the drying heat duty was measured in real time based on the heat supply to maintain isothermal operation.

The heat supplied by the inductive heater was lost in two sources: (1) to the environment through the device's walls, lid, and base, and (2) consumed for solvent evaporation. As the drying step progressed, less solvent was present inside the device and the heat duty to maintain isothermal operation decreases. Eventually, this heat duty equilibrated to a relatively constant value, corresponding to the heat that is being lost to the environment. This parameter was subject to fluctuations in room temperature and device sealing, but those variations are negligible compared to the variations caused by solvent evaporation. By tracking the heat supplied to the device, and with knowledge on how much heat is lost to the environment, the dry matter content of the cake was assessed in real time. This was validated experimentally for two API loads in runs 1, 3 and 4, as seen in Table 1 above.

Figure 8A:
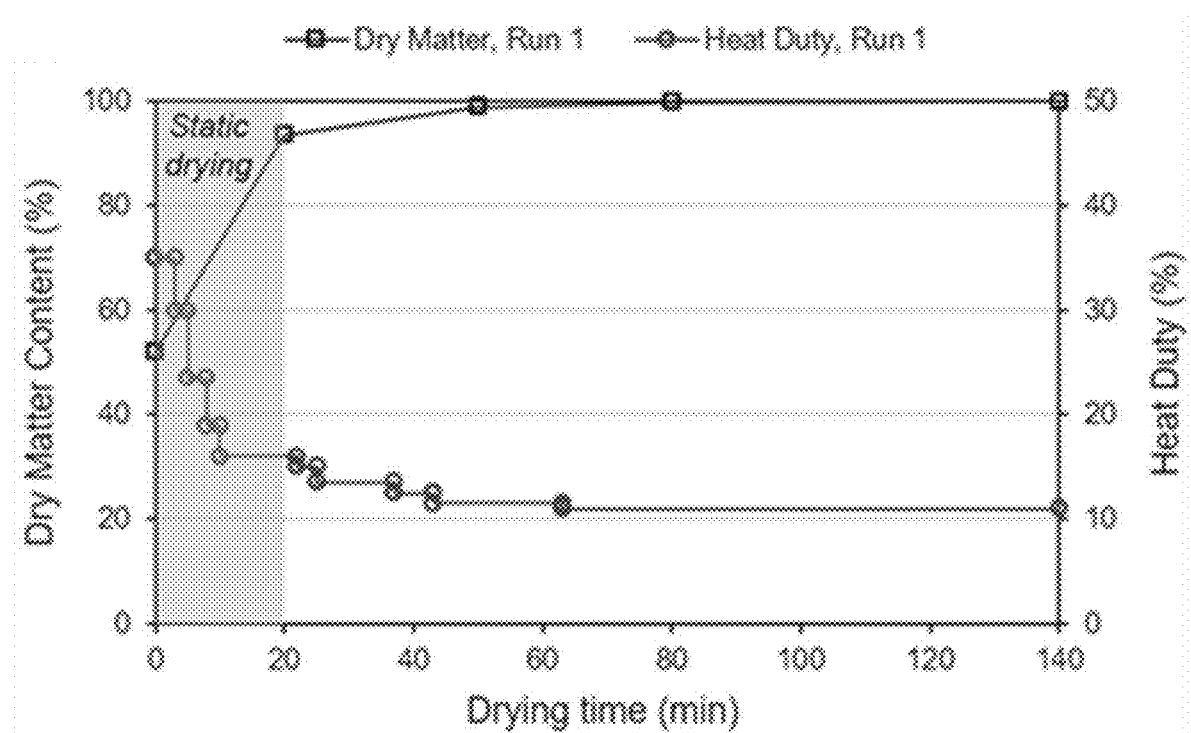
FIGS. 8A-8B show dry matter and heat duty trends during the drying process for 28 g API load (a) and 35 g API load (b), according to some embodiments.
Figure 8B:
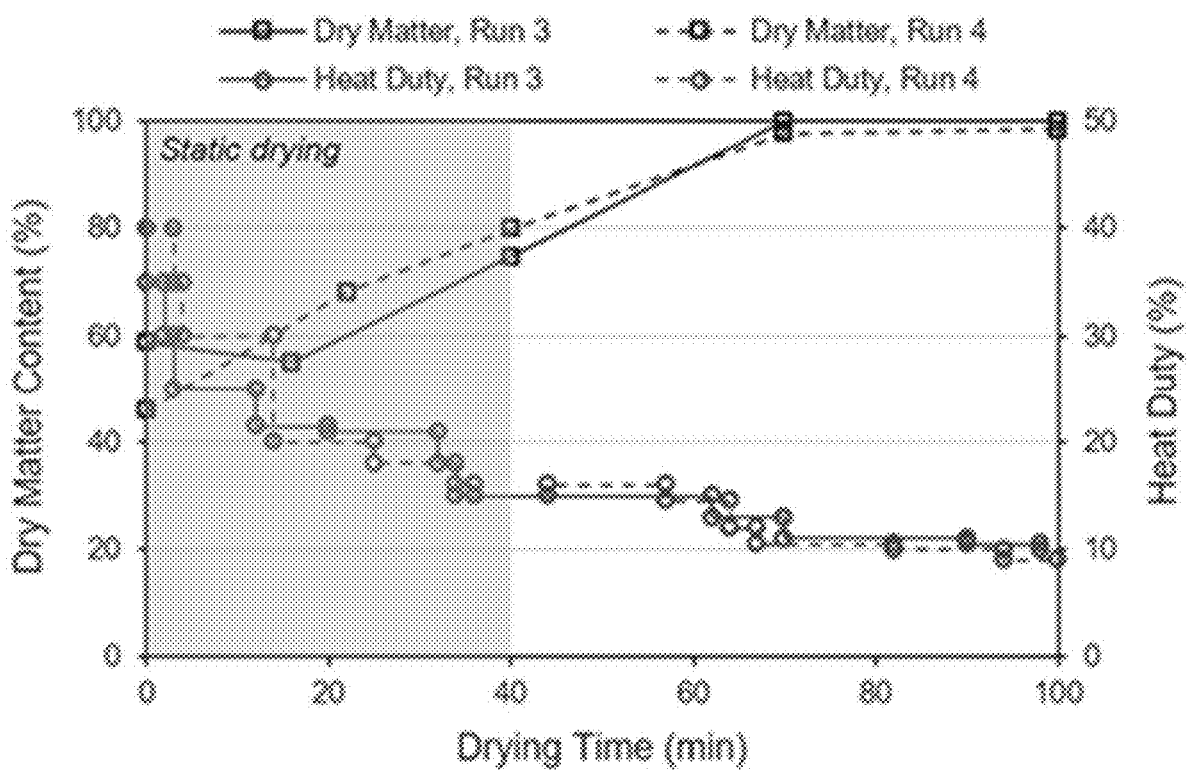

The obtained heat duty trends were plotted together with the dry matter content measurements in FIG. 8. Here, the heat duty is expressed as the percentage of time, in a 2 s period, by which a constant power is being supplied to the inductive heater. In other words, for a heat duty of 40%, heat was supplied for 0.8 s and the power supply was stopped for the remaining 1.2 s. This 2 s cycle was repeated indefinitely until the temperature deviates from 50° C. by 2° C. or more. Then, the time percentage was corrected to account for the change in heat duty.

As expected for lower API loads, the drying time is shorter for run 1. This is due both to the lower amount of solvent and the reduced cake thickness. A common behavior for the three runs is the drop of heat duty at a proportional rate with the drying rate. Furthermore, the three runs ended at approximately 11% heat duty, showing a reproducible value for the environment heat loss regardless of API load. To determine the range of heat duties that corresponds to the desired dry matter content to start delumping (70-80% dry matter for 35 g API load, based on Table 1), the heat duty values were plotted together with the corresponding dry matter contents in FIG. 9.

Figure 9:
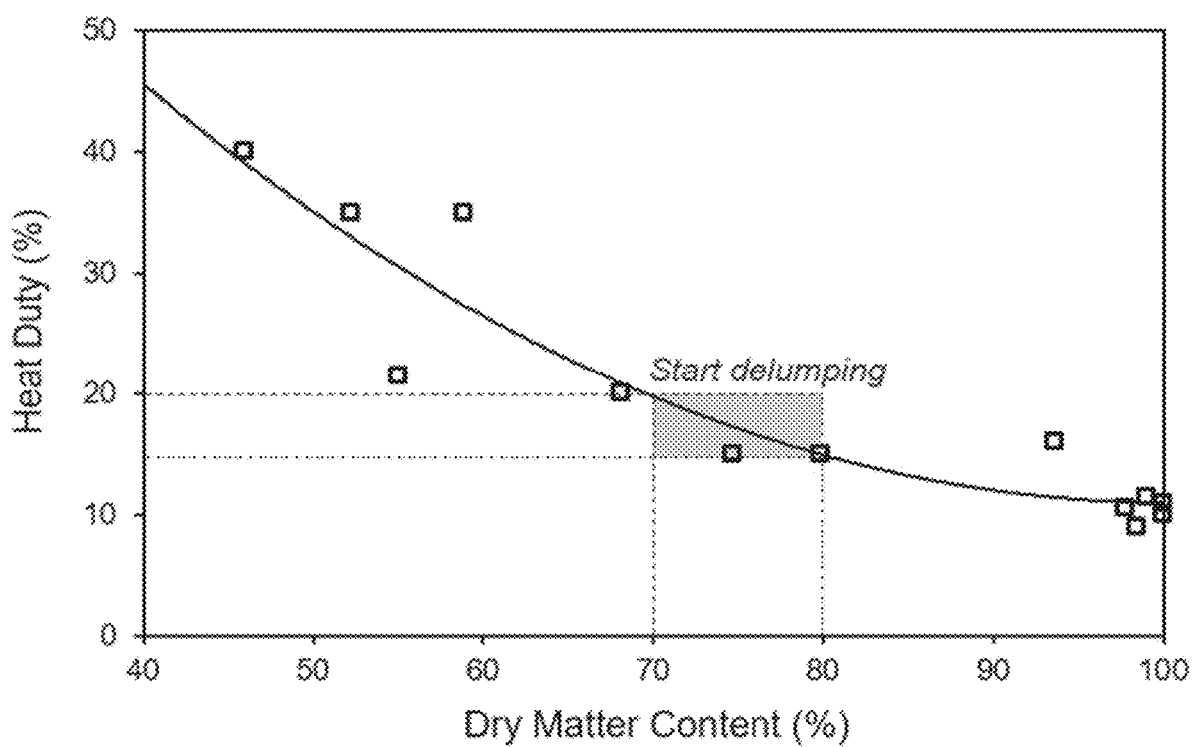
FIG. 9 illustrates a relationship between cake dry matter content and drying heat duty for 35 g API loads, according to some embodiments.
Figure 10:
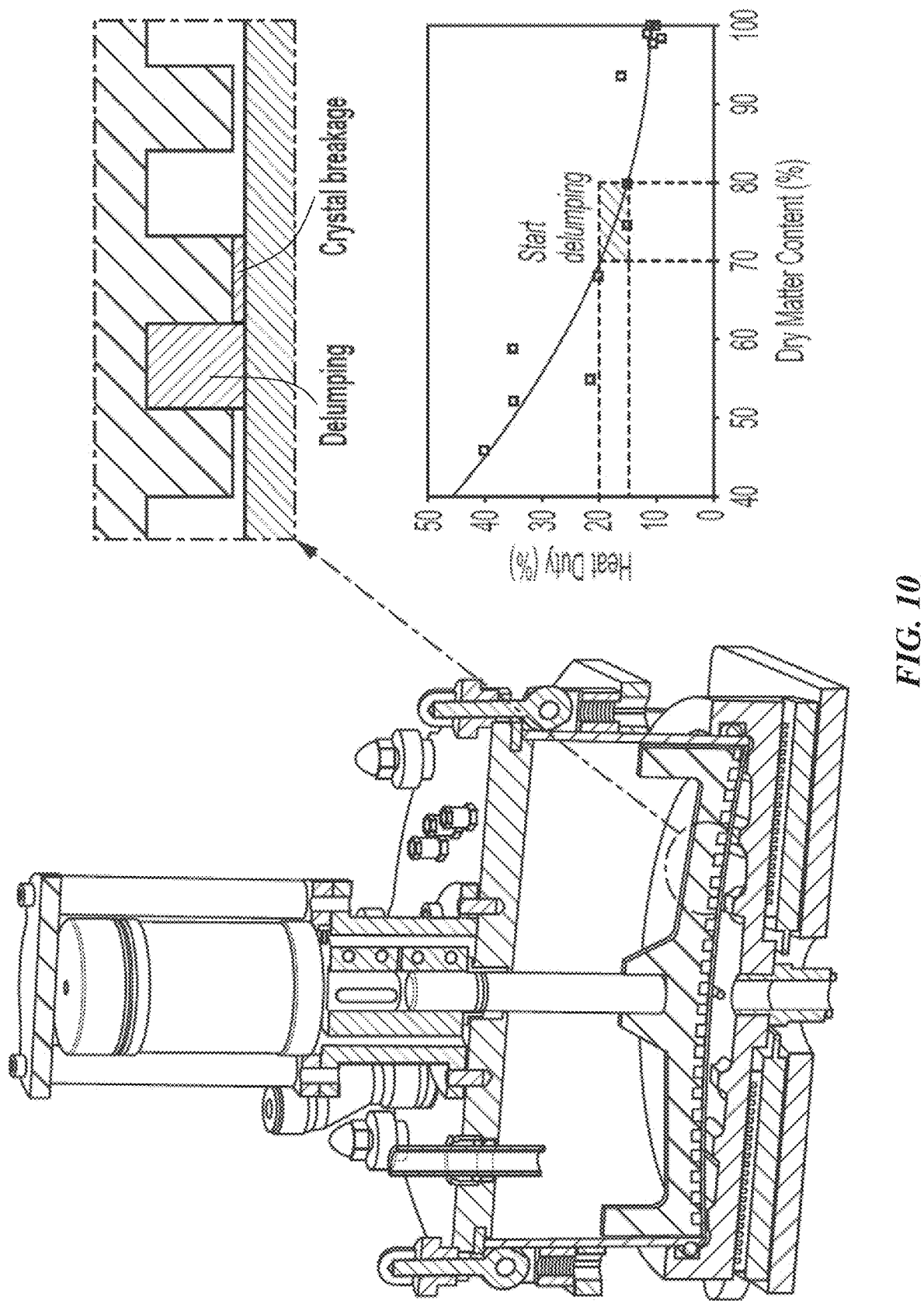
FIG. 10 shows a schematic of a filtration device, according to one set of embodiments.

In a process environment, the heat duty curves in FIG. 8 can be compared with the dry matter relationship in FIG. 9 to assess the dry matter content of the cake in real time. This poses a significant advantage to ensure batch-to-batch consistency, as any fluctuations in drying times could be detected in situ, and the drying times could be corrected before the batch is lost. Nevertheless, note that the relationship between heat duty and dry matter content will vary with the chosen wash solvent, and the heat loss to the environment is subject to variations from the sealing level in the device (i.e., how much air flows through the device). Despite these limitations, this drying curve requires only 1-2 trials to obtain, so it was a very simple process development approach for a new system. For this compound, a feedback control will be implemented during manufacturing, by which the impeller will automatically start delumping after a heat duty below 20% is sustained for 5 minutes. Then, the delumping process will be sustained for 60 min. As it was demonstrated in this example, the material was stable for drying times of at least 140 min, ensuring that batch-to-batch variations in drying time will not impact the quality of the final product.

Example 2

This example describes a system in which a filtration device in accordance with certain embodiments has been integrated into a tablet-manufacturing process.

The materials used in this Example, along with their specific functions and physical properties, are presented in Table 2 below:

TABLE 2

Materials used, in Example 2, for making CIPRO tablets and their properties.

| Name of Ingredient | Quantity (mg) | Percentage Composition (% w/w) | Function | Particle size (μm) | | | Bulk density (g/cm$^3$) | Compressibility (%) | FFC[3] |
|---|---|---|---|---|---|---|---|---|---|
| | | | | $d_{10}$ | $d_{50}$ | $d_{90}$ | | | |
| Ciprofloxacin HCl (CIPRO)[1] | 291.002 | 58.20 | Active Ingredient | — | — | — | g/cm$^3$ | — | — |
| Silicified microcrystalline cellulose | 189.00 | 37.80 | Diluent | 38.83 | 127.61 | 324.56 | — | 6.17 | >10 |
| Fumed silica | 5.00 | 1.00 | Glidant/Flow aid | — | — | — | 0.52 | — | — |
| Magnesium stearate | 5.00 | 1.00 | Lubricant | 2.76 | 6.86 | 15.10 | — | 38.97 | 5.18 |
| Sodium starch glycolate | 10.00 | 2.00 | Disintegrant | 23.62 | 45.67 | 80.27 | 0.31 | 19.0 | >10 |
| Total | 500 | 100 | | | | | — | | |

[1]Monohydrate
[2]Amount reflects conversion from monohydrate salt form to the free base (250 mg)
[3]Flow function coefficient Ciprofloxacin Hydrochloride Monohydrate (CIPRO) was studied as the model drug. The choice of excipients in the design of a drug product was typically based on several criteria (bulk density, compression, biopharmaceutical properties) including stability/target shelf life. Stability enhancement excipients were not considered. A simplified approach in formulation development was considered by minimizing number of excipients required for tableting. Hence, only one filler/diluent, flow aid/glidant and lubricant were considered as part of the formulations. Silicified microcrystalline cellulose (Prosolv SMCC® HD 90) was used as the filler/diluent, fumed silica (CAB-O-SIL® M-5P) was used as the Glidant, and Magnesium stearate (Kosher Passover HyQual™) was used as the lubricant. Sodium starch glycolate (EXPLOTAB®) was used as disintegrant to improve the disintegration of CIPRO tablets as CIPRO tablet is a high volume dosage form which requires higher compaction force than the reported earlier work with the drugs used in the unit.

Characterization and understanding of the particle and bulk properties of the API, the excipients, and blends were important in the development and manufacturing of pharmaceutical formulations and finished products. Size, shape, bulk density and flow properties of CIPRO, excipients (specifically fillers), and blends were characterized to assist in formulation development. The particle size of CIPRO and excipients were measured in the Scirocco 2000, dry powder dispersion unit of Mastersizer 2000 particle size analyzer (Malvern Instruments Ltd.). CIPRO or excipient was placed in the enclosed vibratory tray of Scirocco 2000. The Scirocco 2000 uses compressed air to transport and suspend the particles of the sample while they pass through the air cell. The vibratory tray of Scirocco 2000 was vibrated to feed the powder at the 50% feed rate setting. The powder was dispersed through the air cell at an air pressure of 2 bar. The Mastersizer 2000 reported volume-weighted particle sizes. The median size of fumed silica CAB-O-SIL® M-5P is about 14 nm. The images of the CIPRO were captured with a Nikon optical microscope (model: Eclipse ME600) and are shown in FIG. 14.

Bulk density and powder flow measurements of CIPRO, excipients, and blends were carried out using the FT4 Powder Rheometer (Freeman Technology, Tewkesbury, UK). The bulk density was measured using the conditioned bulk density test, performed before any other test in the FT4. Powder flow property was measured using the shear cell test. The compressibility of the powders under investigation was also measured. Bulk density is an important parameter for determining the amount of powder that can fit in space such as blender, hopper of a tablet press or a tablet die. The shear test yields various powder flow measurements including a flow coefficient. The flow function coefficient (FFC) is used as an indicator of the flowability of a powder and is defined as the ratio of the major principle stress to the unconfined yield strength. The FFC was obtained using a normal stress of 3 kPa. FFC values can be separated into different regimes: FFC<1, not flowing; 1<FFC<2, very cohesive; 2<FFC<4, cohesive; 4<FFC<10, easy flowing, and FFC>10, free-flowing. Powder compressibility was also measured. Compressibility is not a direct measurement of flowability; however a free-flowing powder usually has a low compressibility value. A compressibility value greater than 30% indicates poor powder flow.

The upstream process crystallized CIPRO as needle shaped particles. The product obtained from the crystallizer after drying was a lump. This lump is not suitable for processing through the tablet manufacturing unit. Hence, a delumping step was added. Because no suitable commercial equipment was found for delumping small amounts of powder, a mortar-pestle, Krups grinder and a customized grinder were used. The customized grinder was a compact device designed for the integrated filtration, drying and mechanical processing of active pharmaceutical ingredients. This also assisted in grinding the needles of CIPRO powder. After delumping and grinding, CIPRO was sieved using 600 μm sieve. The head-in-blend dispensing unit (tapping feeder) had an opening hole of 700 μm. Hence, sieving was done using 600 μm. The obtained powder was used for on-demand tablet manufacturing in the compact system.

Tablet properties such as weight, assay, content uniformity, tensile strength, and dissolution performance were evaluated following USP39-NF 34 official monographs during the characterization.

For the CIPRO assay, a mobile phase was prepared at a ratio of acetonitrile to solution C at 13:87. Solution C was 0.025 M phosphoric acid having pH of 3.0±0.1 adjusted by triethylamine. The sample solution was prepared using 5 tablets in solution B in a 500-ml volumetric flask. The solution was filtered through a 0.45 μm filter and diluted to prepare the equivalent of the concentration of 0.2 mg/ml. Solution B was prepared at a ratio of acetonitrile to solution A at 13:87. Solution A was 0.025 M phosphoric acid having pH of 2.0±0.1 adjusted by triethylamine. The UV detector was set to 278 nm. The column was a Supelco Analytical Ascentis® C8 4.6 mm×25 cm, 5 μm with L1 packing, and was maintained at the temperature of 30±1° C. The injection size was 10 μL with a mobile phase flow rate of 1.5 mL/min.

To ensure consistency, each tablet in a batch should have a drug substance content within an 85%-115% of the labeled content, which is considered as 100%. The uniformity can be demonstrated by either of the two methods: content uniformity or weight variation (USP-39 <905> Uniformity of Dosage Units). The weight variation method needs to be followed for uncoated tablets containing 25 mg or more of a drug substance comprising 25% or more, by weight, of the tablet. The content uniformity method needs to be followed in the case the weight variation method does not meet the requirements. In this Example 2, CIPRO were tested by weight variation method. 10 tablets for each drug were assayed individually using the assay methods described above. Acceptance value (AV) was calculated using USP <905> Uniformity of Dosage Units, where an AV of 15 or less should be obtained.

Tablet dissolution was performed according to the USP II paddle method using a Varian VK 7025 dissolution apparatus (Varian, Inc., USA). Dissolution conditions were chosen following USP 39-NF 34 official monographs. The dissolution medium was 900 ml: 0.1 N hydrochloric acid for CIPRO. The paddle rotational speed was 50 rpm. The temperature was maintained at 37° C.±0.2° C. Tablets were added to the dissolution media manually. The UV measurements were obtained using an automatic Varian UV-Vis Cary 50 apparatus and in situ probe set at 276 nm for CIPRO. Dissolution was measured for a total of three tablets.

A customized miniature automated on-demand tablet manufacturing unit was developed. FIG. 11A shows the unit and different miniature pharmaceutical unit operations such as different feeders for API and excipients, filtration device, tapping feeder for dispensing powder blend, tablet press etc. Each component is plug-play type and can be easily assembled and disassembled. An enclosure was used for the solids module to prevent airflow that may cause weighing cell fluctuation, the transfer of solids/dust (if any generates) to the environment. FIG. 11B shows the process flow diagram (PFD) which represents the general flow of the process and equipment. There were five volumetric feeders (Orbetron 50 series micro feeder, OD50SV) mounted in the feeder array. In this example, four feeders were used. Each feeder consists of feeder housing, disc (50 mm in diameter, 10 pocket open hole), powder discharge chute having adafruit vibrating mini motor disc, and hopper (FIG. 11). To improve cohesive powder flow, 18 g of 5 mm glass beads were added in the feeder and $SiO_2$ was premixed with the drug powder. The beads help to break the powder compact when disc rotates and enhance the powder flow. All feeders feed the materials on the powder carriage which transfer the powder into the blender. The amount of materials used for blending is based on the percentage composition given in the above table and the total blend mass.

Figure 12A:
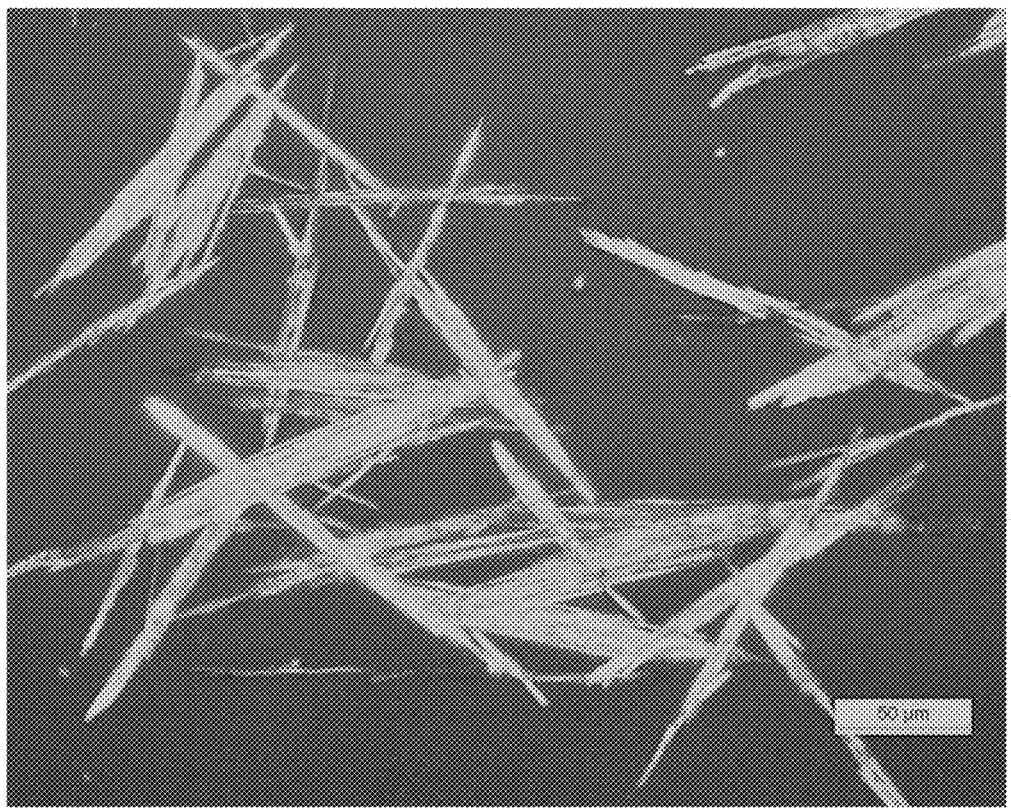
FIGS. 12A-12F show optical microscopy images of Ciprofloxacin HCl (CIPRO) crystal particles: (a) as crystallized needle shaped CIPRO from an upstream process; (b) produced with ultrasound; (c) ground with ultrasound and a mortar and pestle; (d) ground with ultrasound and a Krups grinder; (e) ground with a grinder in accordance with certain embodiments; and (f) as commercially available, according to one set of embodiments.
Figure 12B:
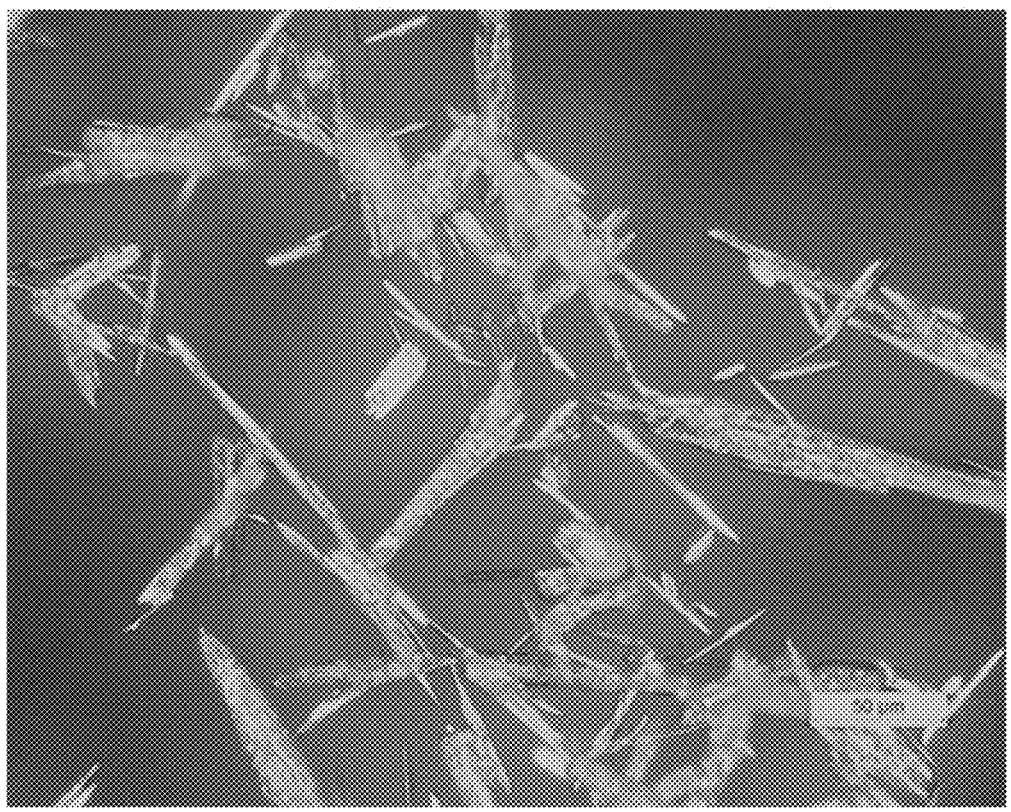

Powder flow properties such as size, shape, bulk density, and the like impacted the feeder performance. The above Table 2 shows material compositions that were used for making CIPRO tablets and their flow properties. The CIPRO crystallized in the crystallizer and had a long, needle-shaped with a high aspect ratio (FIG. 12A) and was very fluffy. Hence, it was not suitable to use through the unit and its flow properties were not measured. Similarly, the flow properties of nano silica, CAB-O-SIL® M-5P were not measured as due to its very fluffy nanosize. The reported average size is about 15 nm. Comparing the flow properties of all excipients, magnesium stearate had a finer particle size, low bulk density, high compressibility, and low FFC. In general, when particle size increases, powder flowability increases, and weaker interparticle force between particles were observed in addition to a decrease in cohesiveness of the powder. Once the powder density increased, the powder packed in a denser state due to the increase in the particle size. Based on Schulze classification both, Prosolv SMCC and EXPLOTAB are free-flowing, whereas, magnesium stearate flows easily; hence, all excipients powders were easily handled through the feeders.

Figure 12C:
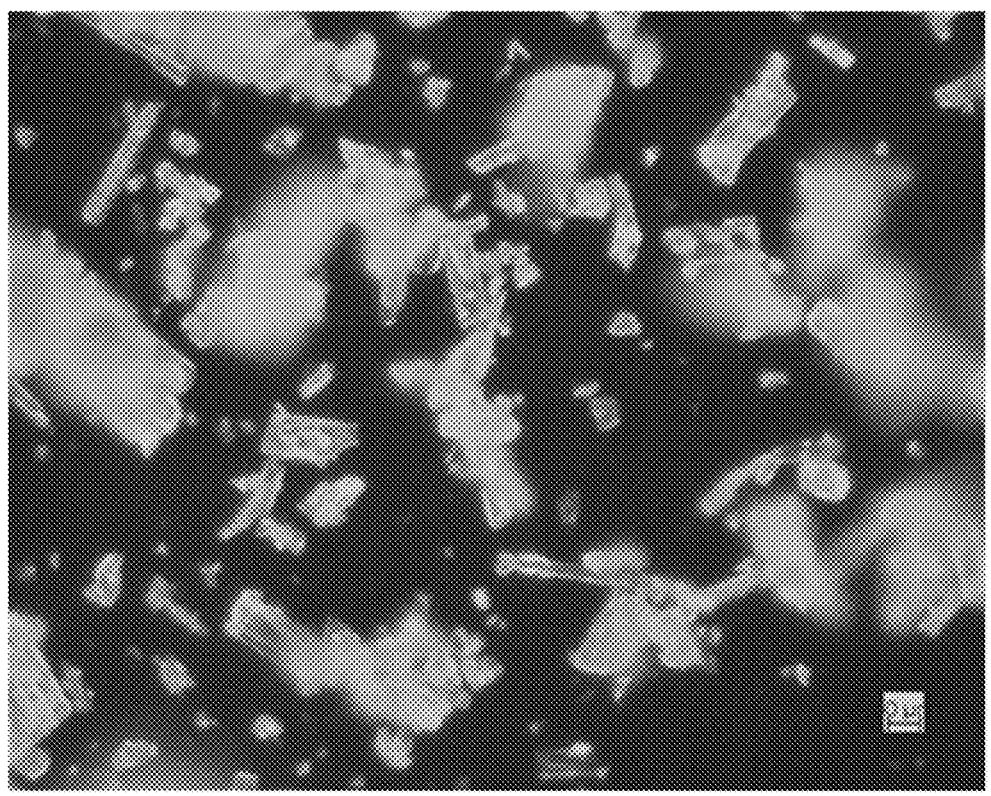
Figure 12D:
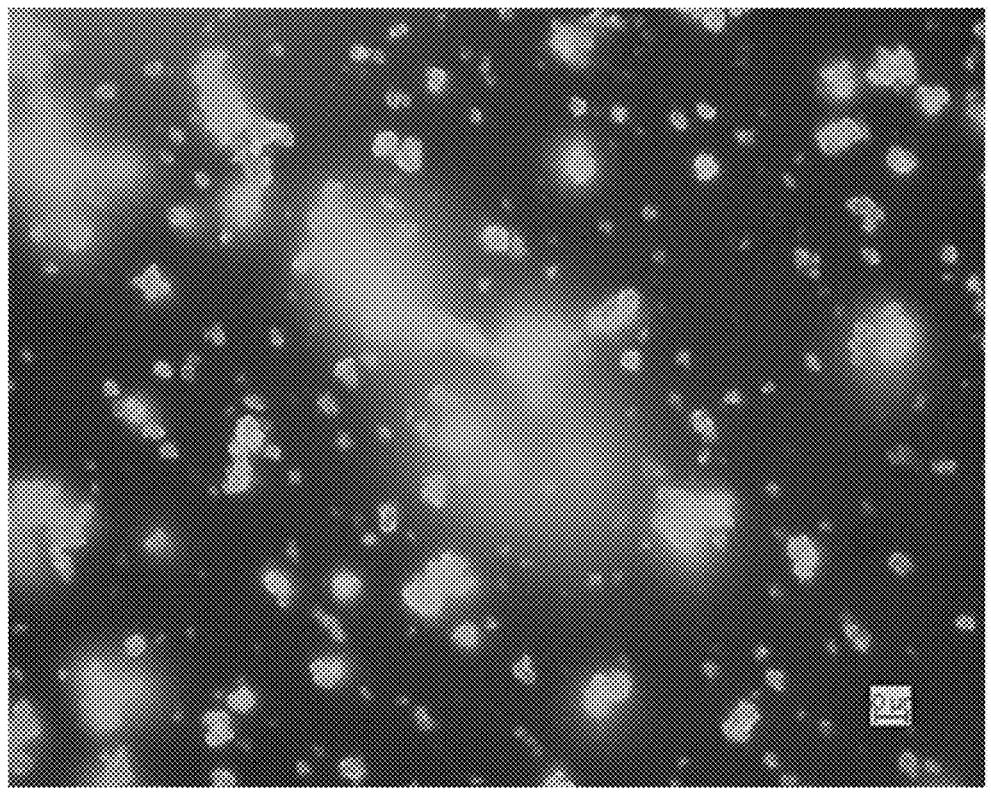
Figure 12E:
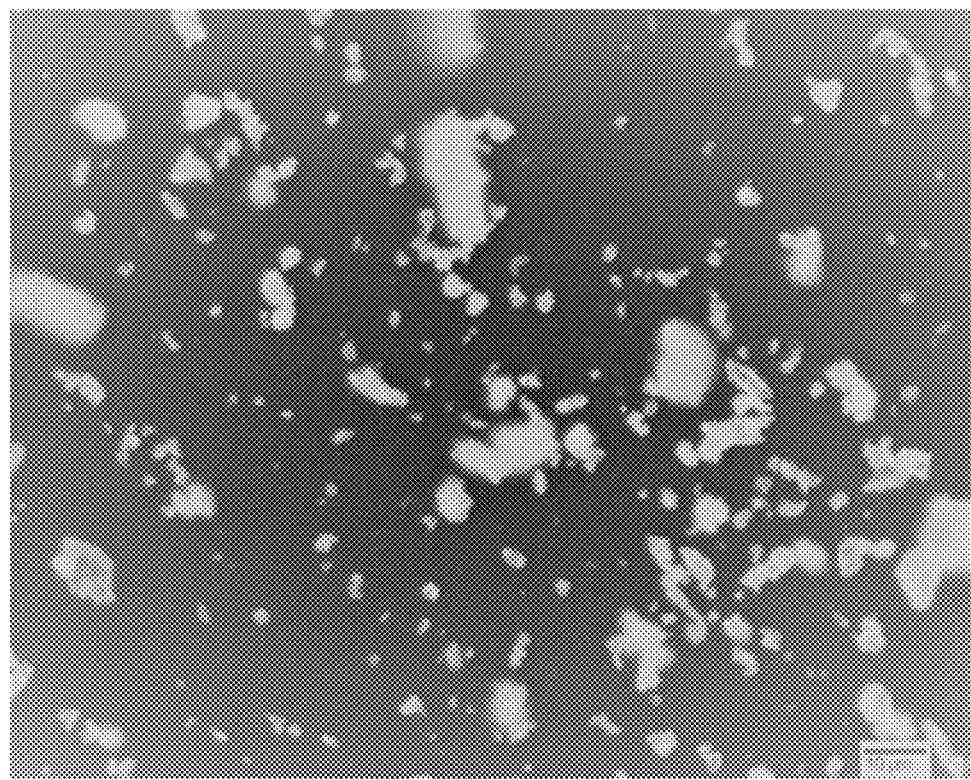
Figure 12F:
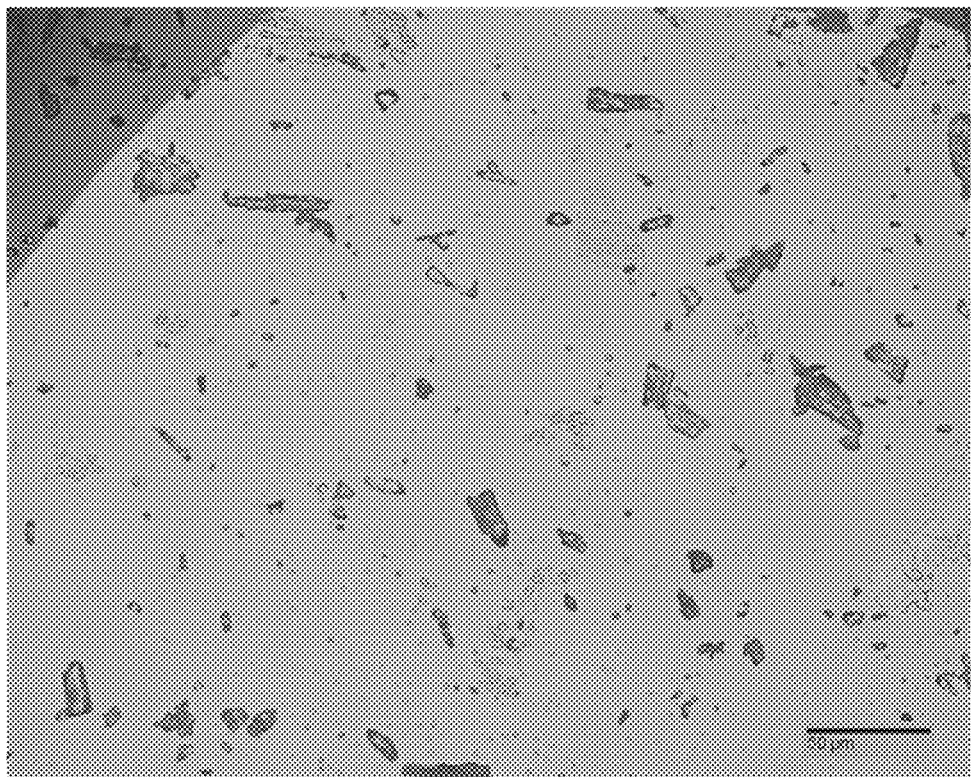
Figure 13A:
FIGS. 13A-13B show photographs illustrating non-limiting examples of processing issues observed due to needle shaped CIPRO.
Figure 13B:

Needle-shaped CIPRO had a very low bulk density, so it occupied a large volume per unit mass. To improve the bulk density as well as the flow behavior, the needles of CIPRO were broken using ultrasound during crystallization. Ultrasound helped to break up the crystals but was unable to completely eliminate all particles that were needle shape (FIG. 12). Therefore, the CIPRO was grounded using a Krups grinder. The CAB-O-SIL premix CIPRO was then processed through the Orbetron feeder. However, the particles were not able to feed through the feeder after the first one or two minutes. They formed compact masses, which prevented free flow of the powder. FIG. 13A illustrates the feeder after the powder flow stopped. Since the pre-mix CIPRO did not flow through the Orbetron feeder, it was added into the blender manually. The powder blend was prepared and dispensed into the tap feeder. After a few taps of dispensing, the blended powder stopped flowing. The blended powder became compacted, which impacted the flow of the powder, which eventually came to a stop. FIG. 3B shows the tap feeder after the powder flow stopped. This behavior can be easily correlated with the flow properties found in FT4 measurement and presented in Table 3 and Table 4 below.

TABLE 3

Properties of processed CIPRO particles in Example 2.

| API, Excipients* | Particle size (μm) | | | Bulk density g/cm³ | Compressibility (%) | Flow function coefficient (ffc) |
| --- | --- | --- | --- | --- | --- | --- |
| | $d_{10}$ | $d_{50}$ | $d_{90}$ | | | |
| CIPRO (w/o US, Krups Grinder) | 1.23 | 3.88 | 33.26 | 0.22 | 52.6 | 1.26 |
| CIPRO (US & Krups Grinder) | 1.93 | 7.09 | 65.36 | 0.38 | 38.8 | 1.56 |
| CIPRO (US & Morter-Pastle) | 3.01 | 8.67 | 24.02 | 0.41 | 43.6 | 2.04 |
| CIPRO (w/o US, Grinder designed at MIT) | 2.82 | 14.45 | 169.73 | 0.48 | 29.5 | 4.17 |
| CIPRO (Commercial, un-processed) | 3.75 | 12.49 | 439.56 | 0.39 | 38.9 | 2.95 |

*US: Ultrasound applied during crystallization

TABLE 4

Properties of powder blends prepared for tableting in Example 2.

| Blends* | Bulk density g/cm³ | Compressibility (%) | Flow function coefficient (ffc) |
| --- | --- | --- | --- |
| CIPRO (w/o US, Krups Grinder) | 0.44 | 32.5 | 2.06 |
| CIPRO (US & Krups Grinder) | 0.55 | 23.0 | 2.41 |

TABLE 4-continued

Properties of powder blends prepared for tableting in Example 2.

| Blends* | Bulk density g/cm³ | Compressibility (%) | Flow function coefficient (ffc) |
| --- | --- | --- | --- |
| CIPRO (US & Morter-Pastle) | 0.51 | 23.2 | 4.67 |
| CIPRO (w/o US, Grinder designed at MIT) | 0.57 | 12.4 | >10 |
| CIPRO (Commercial, Un-Processed) | 0.69 | 21.1 | 8.25 |

*US: Ultrasound applied was applied during crystallization.

It was apparent upon considering the data from Table 3 that CIPRO (w/o use of a Krups Grinder) had a low bulk density 0.22 (as mentioned previously) and an FFC of 1.26, and a high compressibility of 52.6. Similarly, blended CIPRO also had a low bulk density and FFC, and a high compressibility. Hence, CIPRO powder and blended CIPRO had very poor flow behavior. These overall findings demonstrated that particle shape had an impact on pharmaceutical unit operations even it is on a miniature scale.

Only when applying ultrasound during the crystallization process or by using a Krups grinder for the crystallized CIPRO did the flow properties improve. Hence, both of these processes were combined and applied. CIPRO was grounded using either Krups grinder or mortar and pestle. A mortar and pestle can handle a small mass of materials and it can apply a gentle shear. However, its operation is biased due to human handling, which is not efficient for handling a large amount of CIPRO in a high volume dosage. A Krups grinder can handle a large amount of CIPRO but it only works at one speed. It also applies high stress compared to a mortar and pestle. However, both mortar and pestle and Krups grinder may help with delumping. The properties of CIPRO ground using Krups or mortar and pestle are given in Table 3 above. Comparing to CIPRO particles grounded with Krups grinder or mortar and pestle, no difference in flow properties was observed. The bulk density and compressibility were also in the same range. The optical microscopy of CIPRO particles is shown in FIG. 12C-12D. The image shows that while particle size was reduced, the needle shape was not able to completely eliminate even applying the combined process. Comparing to Krups ground particles, mortar and pestle ground particles have longer needle-shaped particles (FIGS. 12C-12D). This is due to low shear applied to particles by mortar and pestle. The comparison of powder blends of both types of blend shows no significant difference in flow properties.

The combined approach was not able to improve powder flow properties and not suitable for dispensing and subsequently tableting. Hence, the filtration device described herein for integrated filtration, drying, and mechanical processing of APIs was used. FIG. 14 shows schematic and the filtration device itself, respectively. CIPRO powder produced using this filtration device described herein shows high bulk density (0.48) and FFC (4.17), and low compressibility (29.5). Comparing all processed powders, powders produced using the filtration device had better powder flow properties (see Table 3). The particle size was slightly larger than other processed particles. The particle size $d_{50}$ and $d_{90}$ are larger when using the filtration device described herein. The particle shape was observed by optical microscopy and is shown in FIG. 12E. No long, needle-shaped particles observed, in contrast to when CIPRO was processed using a only a Krups grinder or only a mortar and pestle. A combination of fine and large particles was observed when using the filtration device. The particle shape of commercially processed CIPRO is shown in FIG. 12F and, it also has a combination of fine and large particles. This corroborates the particle size distribution presented in Table 3. The powder blend was also prepared and characterized by FT4. Blend properties significantly improved when CIPRO was processed using the filtration device described herein was used.

Figure 15:
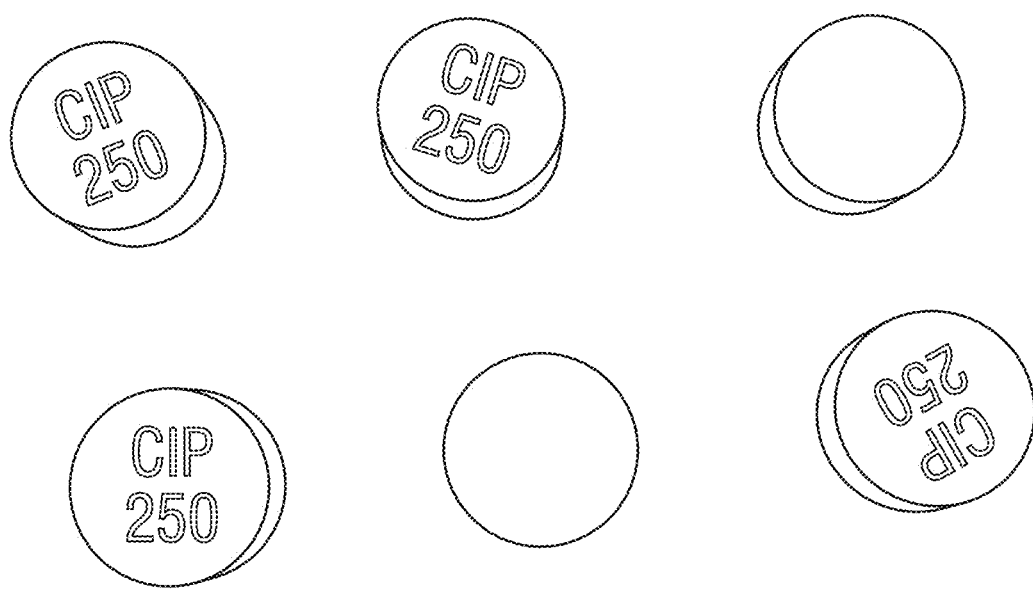
FIG. 15 shows a drawing of CIPRO tablets produced, according to one set of embodiments.

To make compressible tablets directly from the free-flowing CIPRO powder, the powder should have good flow properties, be readily compressible, and have a high bulk density. Large tablet sometimes have undesirable weight variability, poor content uniformity, and inconsistent tablet properties such as a low required breaking force, disintegration issues, and undesirable dissolution if the powder has poor flow. Blend powders produced using CIPRO from the filtration devices and methods described herein showed good flow properties and thus tablets were easily manufactured by using the miniature manufacturing unit seen in FIG. 11A. FIG. 15 shows the picture of tablets produced using the unit shown in FIG. 11A. These tablets were embossed with the letter "CIP 250," as seen in FIG. 15. The average weight of CIPRO tablet was 479 mg and the weight variation was within 10% of the target weight. The RSD value is 5% which indicated a uniform blend dispensed into the die and a low weight variations of the tablets manufactured using this unit. The average tensile strength of the tablet was 4.67 MPa. The average diameter and thickness of six tablets was 10.98 mm and 3.88 mm, respectively. Due to gradual radial recovery during ejection, a slight increase in tablet diameter was observed. The tablet strength depended on the formulation, compositions, and compression forces applied. In Example 2, 1000 kg was the maximum compression force applied by the tablet press.

Figure 16:
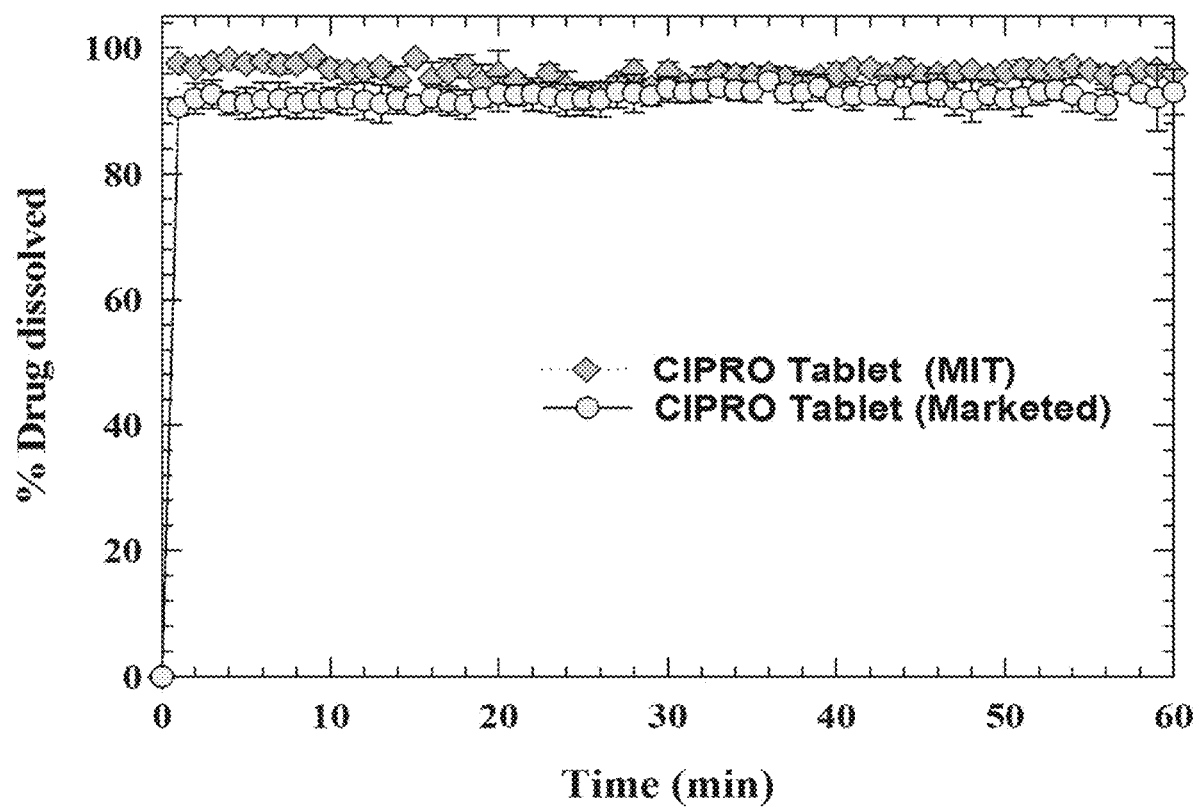
FIG. 16 shows evolution of dissolution of CIPRO tablets after manufacturing and compared with commercially available tablets in a USP II apparatus, according to some embodiments.

Based on USP-39 official monograph, the tablets met the assay standard when the tablets contained not less than 90% and not greater than 110% of the labeled amount. Similarly, the each tablet meet the USP quality standard when the calculated acceptance value of CIPRO is less than or equal to 15.0, based on 10 dosage units. It was observed that the assay value of a CIPRO tablet was within the range, 90-100% and met the content uniformity/weight variation criteria as the acceptance value (AV) was below 15. FIG. 16, the evolution of the dissolution of CIPRO tablets after manufacturing compared to commercially-available tablets in a USP II apparatus is shown. According to USP monograph, 85% of the CIPRO dissolved within 30 mins. The faster dissolution of CIPRO tablets implied instant release tablets. The faster dissolution of CIPRO tablets implies fasted disintegration due to the presence of super disintegrant SSG.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising:
    rotating an edge comprising a plurality of protrusions extending toward a filtration medium such that the edge sweeps at least a portion of a facial area of the filtration medium in a clockwise direction; and
    rotating the edge such that the edge sweeps at least a portion of the facial area of the filtration medium in a counterclockwise direction;
    wherein the edge comprises at least 20 protrusions having a protruding dimension of greater than or equal to 1 mm and less than or equal to 2 cm;
    wherein the at least 20 protrusions have an average spacing of greater than or equal to 1 mm and less than or equal to 1 cm;
    wherein the rotating in the clockwise direction and/or the counterclockwise direction breaks up solid material having maximum cross-sectional dimensions of greater than or equal to 100 micrometers and less than or equal to 10 millimeters, forming a powder; and
    wherein at least 90%, by mass, of the powder has a particle size of less than 500 micrometers.

2. The method of claim 1, further comprising heating a region proximate the edge and the filtration medium during at least a portion of the rotating.

3. The method of claim 1, further comprising establishing a vacuum between the edge and the filtration medium during at least a portion of the rotating.

4. The method of claim 1, wherein the edge and the filtration medium are part of a filtration device, and the method further comprises adjusting a speed of rotation of the edge based, at least in part, on a temperature of at least one component of the filtration device.

5. The method of claim 1, wherein rotating the edge promotes breakage of particles of the active pharmaceutical ingredient.

6. The method of claim 1, further comprising changing the direction of rotation between the clockwise direction and the counterclockwise direction at least 2 times per minute.

7. The method of claim 1, further comprising changing the direction of rotation between the clockwise direction and the counterclockwise direction at least 10 times per minute.

8. The method of claim 1, wherein the rotating in the clockwise and/or the counterclockwise direction delumps aggregates of solid particles.

9. The method of claim 1, wherein the rotating in the clockwise and/or the counterclockwise direction breaks up crystals of active pharmaceutical ingredient.

10. The method of claim 1, wherein the facial area of the filtration medium is less than or equal to 1 m$^2$.

11. The method of claim 1, wherein the powder has a flow function coefficient of greater than 10.

12. A method of processing a cake comprising an active pharmaceutical ingredient, the method comprising:
    rotating an edge comprising a plurality of protrusions extending toward a filtration medium such that the edge sweeps at least a portion of the filtration medium in a clockwise direction; and
    rotating the edge such that the edge sweeps at least a portion of the filtration medium in a counterclockwise direction;
    wherein the rotating in the clockwise direction and/or the counterclockwise direction breaks up agglomerates and/or lumps formed from the cake comprising the active pharmaceutical ingredient, the agglomerates and/or lumps having maximum cross-sectional dimensions of greater than or equal to 100 micrometers and less than or equal to 10 millimeters, forming powder from the cake;
    wherein at least 90%, by mass, of the powder has a particle size of less than 500 micrometers;
    wherein the edge comprises at least 20 protrusions having a protruding dimension of greater than or equal to 1 mm and less than or equal to 2 cm; and
    wherein the at least 20 protrusions have an average spacing of greater than or equal to 1 mm and less than or equal to 1 cm.

13. The method of claim 12, further comprising changing the direction of rotation between the clockwise direction and the counterclockwise direction at least 2 times per minute.

14. The method of claim 12, further comprising changing the direction of rotation between the clockwise direction and the counterclockwise direction at least 10 times per minute.

15. The method of claim 12, wherein the rotating in the clockwise and/or the counterclockwise direction delumps aggregates of solid particles formed from the cake.

16. The method of claim 12, wherein the rotating in the clockwise and/or the counterclockwise direction breaks up crystals of active pharmaceutical ingredient.

17. The method of claim 12, wherein the filtration medium comprises a facial area, and the facial area of the filtration medium is less than or equal to 1 m$^2$.

18. The method of claim 12, wherein the edge and the filtration medium are part of a filtration device, and the method further comprises adjusting a speed of rotation of the edge based, at least in part, on a temperature of at least one component of the filtration device.

19. The method of claim 12, wherein the powder has a flow function coefficient of greater than 10.

* * * * *

UNITED STATES PATENT AND TRADEMARK OFFICE
CERTIFICATE OF CORRECTION

PATENT NO. : 11,911,719 B2
APPLICATION NO. : 16/933158
DATED : February 27, 2024
INVENTOR(S) : David Brancazio et al.

It is certified that error appears in the above-identified patent and that said Letters Patent is hereby corrected as shown below:

In the Specification

At Column 1, Lines 21-24, in the paragraph under the heading "GOVERNMENT SPONSORSHIP":
"This invention was made with Government support under Grant No. HR0011-16-2-0029 awarded by the Defense Advanced Research Projects Agency (DARPA). The Government has certain rights in the invention."

Should read:
--This invention was made with government support under HR0011-16-2-0029 awarded by the Defense Advanced Research Projects Agency. The government has certain rights in the invention.--

Signed and Sealed this
Eleventh Day of June, 2024

Katherine Kelly Vidal
*Director of the United States Patent and Trademark Office*